United States Patent [19]

Kania

[11] Patent Number: 5,653,768
[45] Date of Patent: Aug. 5, 1997

[54] DUAL CANTILEVERED LEAF SPRING STRUCTURE

[75] Inventor: Bruce Kania, 717 S. 14th St., Bozeman, Mont. 59715

[73] Assignee: Bruce Kania, Bozeman, Mont.

[21] Appl. No.: 184,667

[22] Filed: Jan. 21, 1994

[51] Int. Cl.$^6$ ....................................................... A61F 2/60
[52] U.S. Cl. .................. 623/55; 623/27; 623/35; 623/38; 623/49; 623/52
[58] Field of Search ..................... 623/49, 50, 52, 623/55, 27, 35, 38

[56] References Cited

U.S. PATENT DOCUMENTS

| 875,482 | 12/1907 | Wyatt | 623/27 |
|---|---|---|---|
| 4,822,363 | 4/1989 | Phillips | 623/27 |
| 4,959,073 | 9/1990 | Merlette | 623/27 |
| 5,116,381 | 5/1992 | Palfray | 623/50 |
| 5,156,631 | 10/1992 | Merlette | 623/52 |
| 5,181,933 | 1/1993 | Phillips | 623/52 |
| 5,217,500 | 6/1993 | Phillips | 623/52 |
| 5,258,039 | 11/1993 | Goh et al. | 623/52 |

FOREIGN PATENT DOCUMENTS

| 1586704 | 8/1990 | U.S.S.R. | 623/55 |
|---|---|---|---|
| 9410943 | 6/1994 | WIPO | 623/55 |

OTHER PUBLICATIONS

Walking Members for Bilateral Amputation of Thigh Thomas Wheeldon, Apr. 1933.

*Primary Examiner*—John G. Weiss
*Assistant Examiner*—Bruce E. Snow
*Attorney, Agent, or Firm*—Dann, Dorfman, Herrell and Skillman

[57] ABSTRACT

A dual cantilevered leaf spring structure may provide a prosthesis for an amputee or supplement the feel and action of a human foot and lower leg. The structure is provided with separate limb members each attachable at its top shank to a mounting platform. The shanks are preferably rigid, but the limbs become resilient and spring-like as they extend away from their mounting. One limb terminates in a toe piece and the other a heel piece. A stump socket interface provides a mounting platform having a slot receptacle and set screw holders for each shank of a limb permits the point of support to be located high off the ground and permits height and, in some cases, cant adjustment. The use of composite or stranded graphite construction flat oval tubes allows minimal width combined with considerable shaping ability which is particularly desirable for constructing braces or structures providing non-prosthetic augmentation of natural walking, running and jumping movements in shoes or boots.

33 Claims, 15 Drawing Sheets

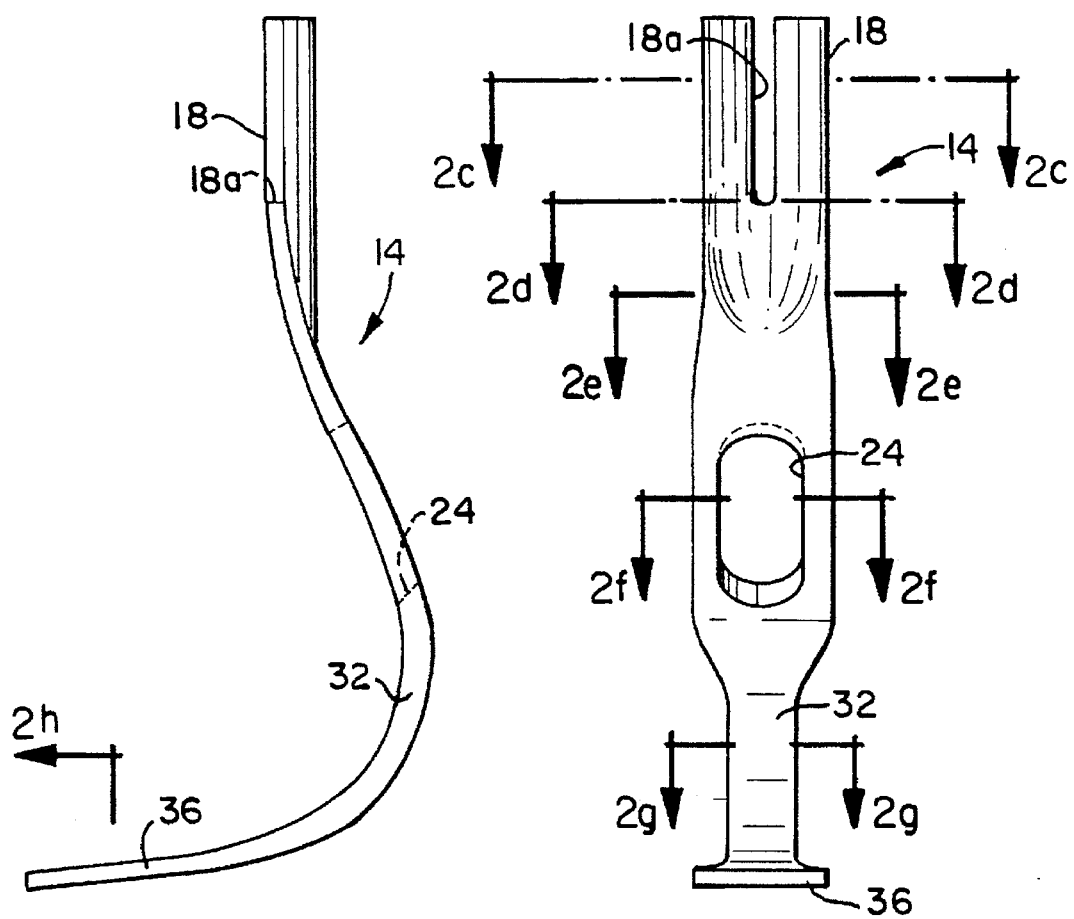
FIG. 2a  FIG. 2b
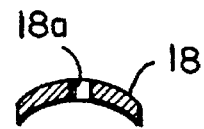
FIG. 2c  FIG. 2d  FIG. 2e
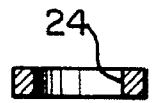
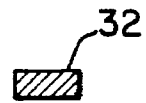
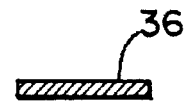
FIG. 2f  FIG. 2g  FIG. 2h

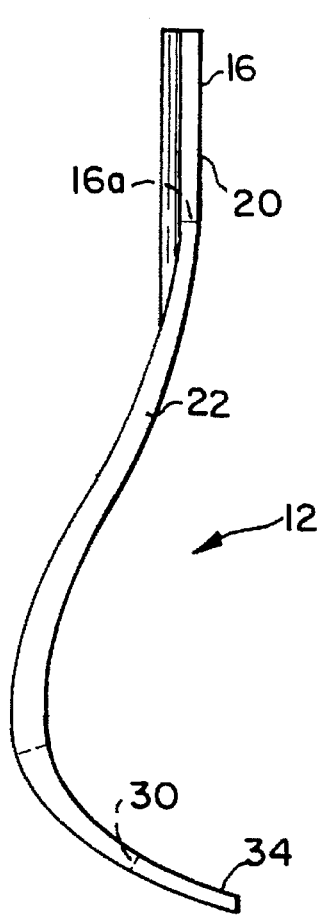
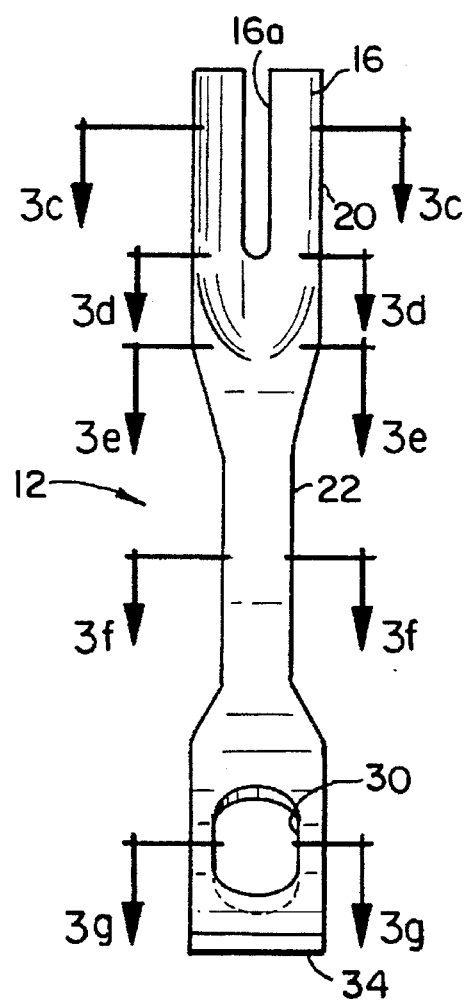
FIG. 3a        FIG. 3b
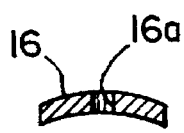  
FIG.3c    FIG.3d    FIG.3e
 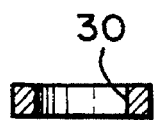
FIG.3f    FIG.3g

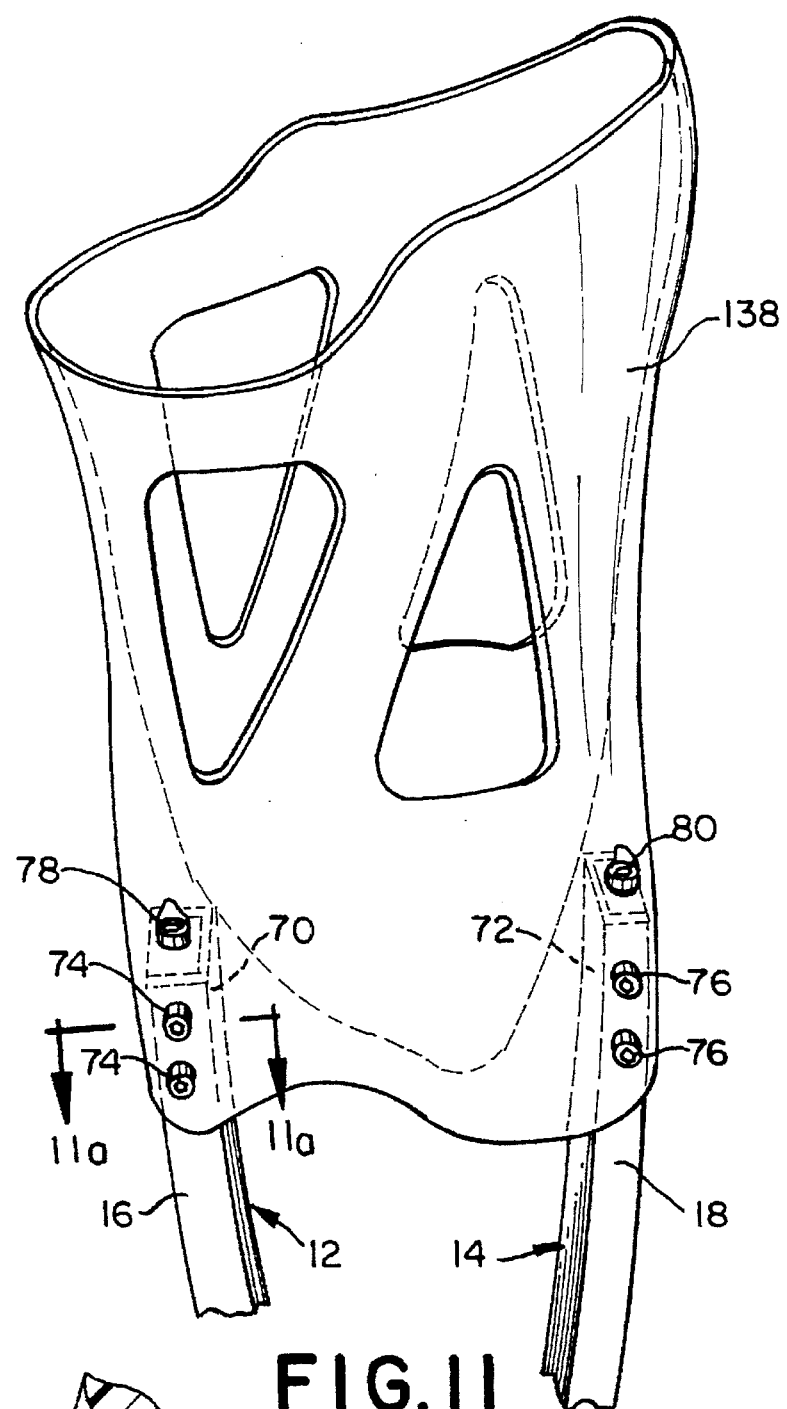
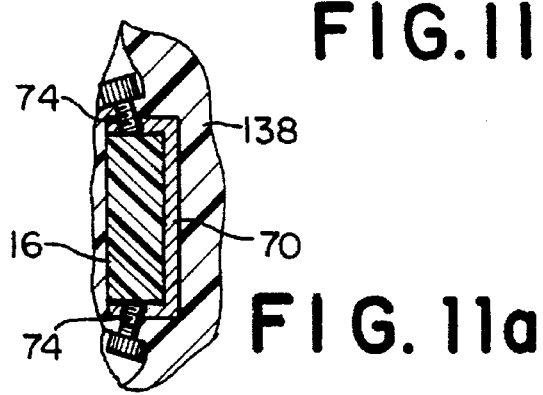
FIG. 11
FIG. 11a

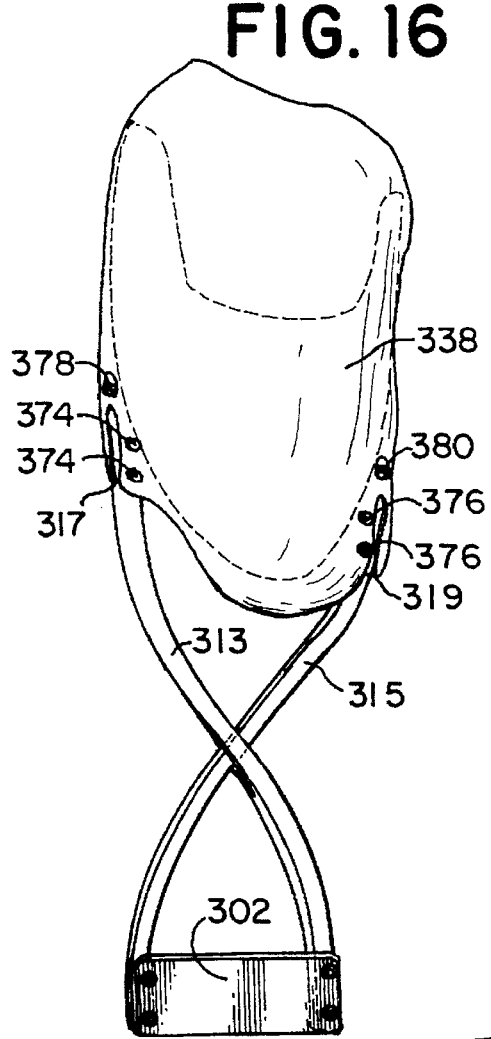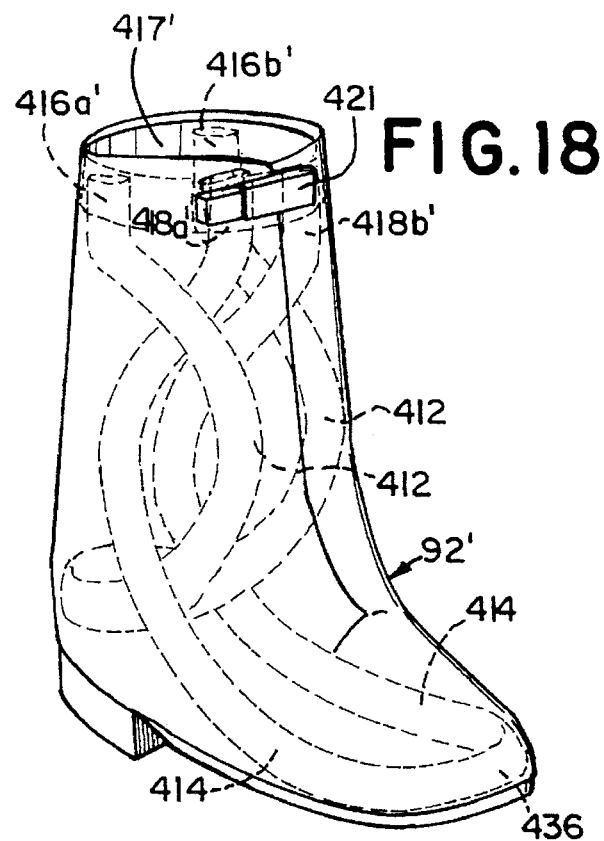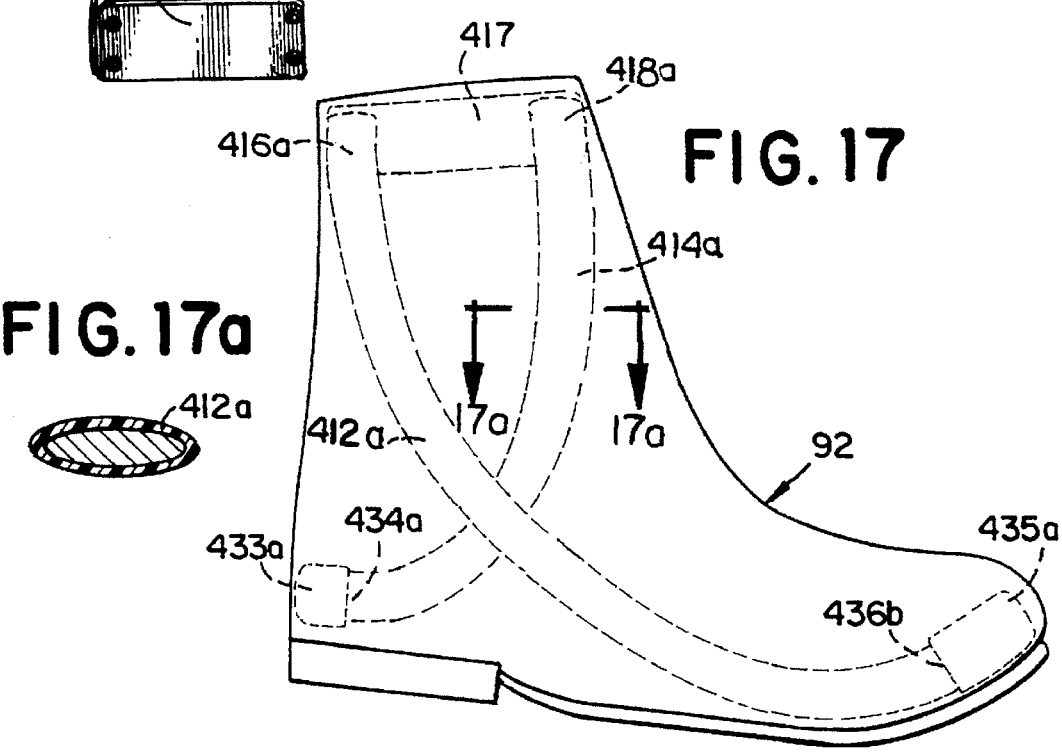

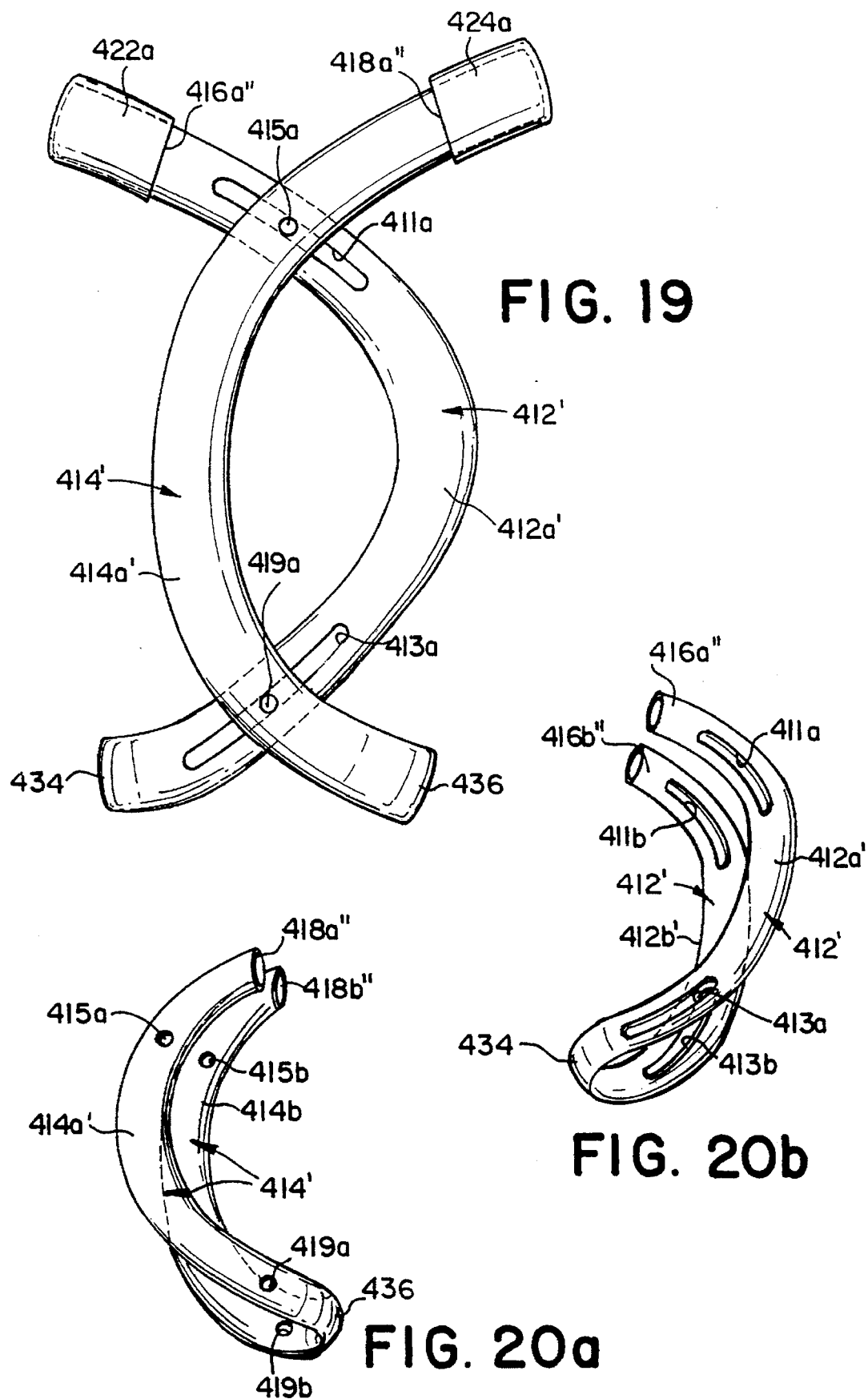

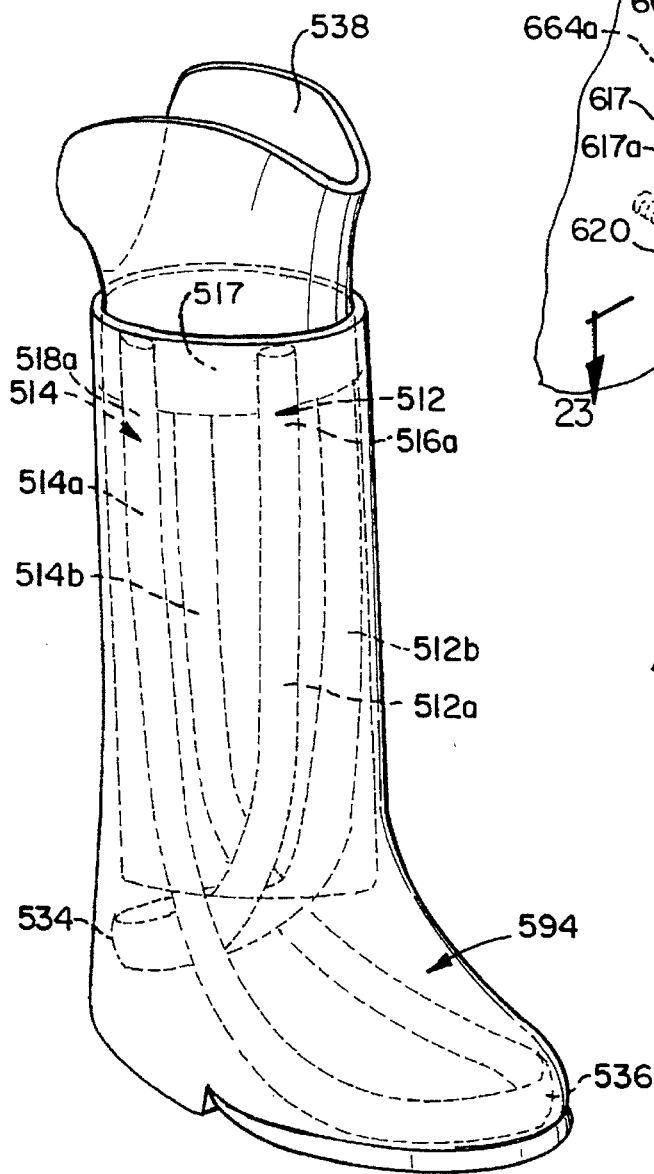
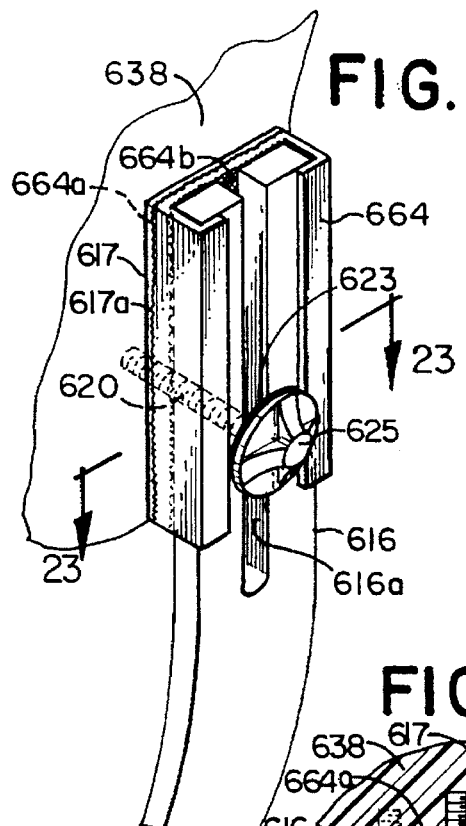
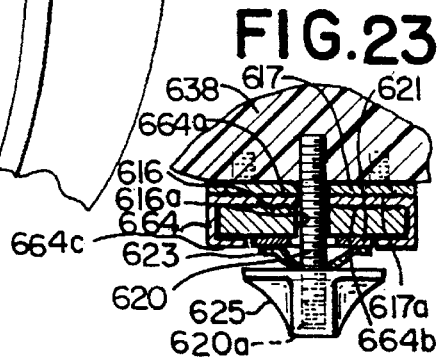
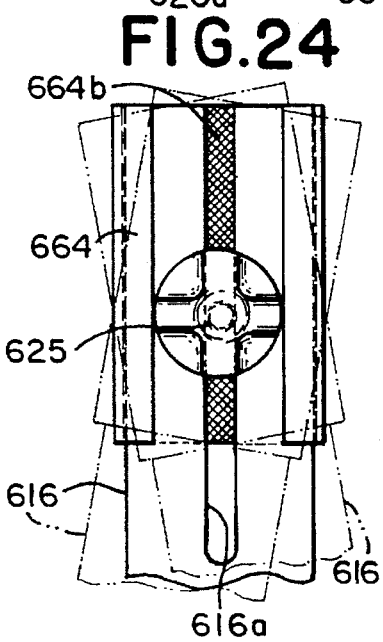

  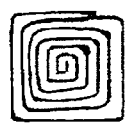  
FIG. 25a FIG. 25b FIG. 25c FIG. 25d FIG. 25e
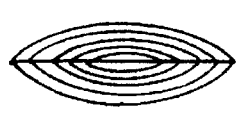   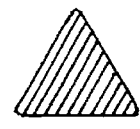 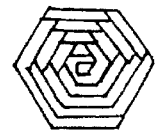
FIG. 26a FIG. 26b FIG. 26c FIG. 26d FIG. 26e
 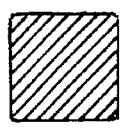 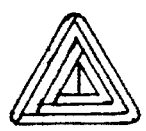 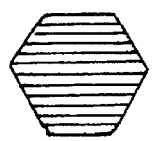 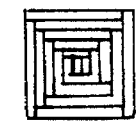
FIG. 26f FIG. 26g FIG. 26h FIG. 26i FIG. 26j
    
FIG. 27a FIG. 27b FIG. 27c FIG. 27d FIG. 27e
    
FIG. 27f FIG. 27g FIG. 27h FIG. 27i FIG. 27j

DUAL CANTILEVERED LEAF SPRING STRUCTURE

The present invention relates to a human foot and lower leg prosthesis simulating the feel and action during walking of a human foot. An upper leg prosthesis or portion thereof is also provided by the present invention. This invention also provides a prosthesis mounting platform for greater comfort to the wearer. The invention provides as well a variety of socket interface and connection concepts to better connect the limbs of the prosthesis of the present invention to the stump socket interface of the amputee. The invention is also applicable to braces for aiding in the support of a weakened lower leg and foot and also may be incorporated into a boot or shoe to enhance the mobility of a person with no disability.

BACKGROUND OF THE INVENTION

The first object of an artificial leg is to supply support means to reach the ground from the stump of the leg of the amputee. The proverbial peg-leg provides support at a certain point or small area on the ground, but does little to replace the feel and action of the amputee's lost foot. It often effects the rest of his body as the result of the abnormal gait it produces.

In the prior art some work has been done to provide prosthetic foot and leg which simulates the feel and action during walking of a human foot. In particular, U.S. Pat. Nos. 4,547,913, 4,822,363 and 5,217,500 to Van L. Phillips, provides a prosthetic foot and leg which, particularly in the foot portion, makes some effort to give resilience to pieces simulating the toe and the heel, respectively, of the prosthetic foot. In those structures a rigid member provides the leg portion, to which resilient add-on members simulating a toe and heel are attached, usually at about ankle level. Typically, the toe and heel pieces each extend from a common junction on a single leg piece.

Instead of a unitary structure, the present invention provides two separate cantilevered members supported from a stump socket interface, or other support, and each of which members acts essentially independently of the other, although in preferred embodiments they may even pass through one another or otherwise place limits on their normal independent action to facilitate lateral stability and in some cases to limit and/or dampen relative movements.

Since the pieces, or limbs, of the present invention are separate and individually affixed to a support, preferably to the socket interface of the stump, for cantilevered support of the member, there is also the possibility of vertical adjustment between the heel and toe pieces. Such adjustments may accommodate the prosthesis to individual comfort and feel or special desires, such as a women wishing to wear high-heeled shoes. Adjustments of both limbs may also be needed with the growth of a child amputee.

The present invention also permits adaptation of the prosthesis to provide not a substitute for a portion of a leg and foot, but rather a brace which extends along side and in planes generally parallel to the leg, although they may follow the contour of the foot. It is possible to position one limb on one side and the other limb on the opposite side of the leg. More frequently, however, pairs of limbs may be located on both sides of the leg.

In other applications, the present invention may be modified to provide a supplement to the action of a foot by incorporating it with or within a shoe.

The present invention also provides a novel mounting platform in the custom socket interface which is specifically molded to fit a particular amputee's stump. The molded socket interface can incorporate part or all of a mounting allowing attachment of the individual limbs directly to the socket interface. Depending on the receiving means for the limbs, this arrangement provides a higher point of attachment of the prosthesis as well as permitting vertical and, in some embodiments, lateral or canting adjustment of the limb.

More specifically, the present invention relates to a prosthesis simulating the feel and action during walking of a human foot and lower leg. A pair of resilient spring-like limbs, part of one of which simulates the toe, and part of the other of which simulates the heel of the foot, are supported on the leg of the wearer. Each of the limbs is composed of a resilient spring material cantilever supported by a support shank on the leg of the wearer, and each of the limbs has a curvature at least in one direction. One limb simulates a toe and front portion of the foot. The other limb simulates the heel of the foot. Both limbs, acting in concert, provide a new level of lift energy, typically at the ankle and possibly also immediately below the amputee's socket interface. In prosthetic use both the toe and front portion and the heel portion can be made broad for stability and yet be designed with flexibility to more truly simulate the action and feel of a real foot. The prosthesis of the present invention provides both terrain accommodation and a biofidelic, fluid motion response in walking simulating natural muscle flexion.

BRIEF DESCRIPTION OF THE DRAWINGS

FIGS. 2a and 2b, respectively, show a side elevation and a front elevation of the limb of the prosthetic device providing the toe;

FIGS. 2c–2h are sectional views taken along FIGS. 2a and 2b at section lines labeled with the suffix of the respective figures;

FIGS. 3a and 3b are a side elevation and a front elevation, respectively, of the other limb of the prosthetic device of FIG. 1 providing the heel;

FIGS. 3c–3g are respectively sectional views taken along section lines of FIG. 3b labeled with the suffix letter of the respective figures;

FIG. 11 is a perspective view of a socket interface attached to prosthetic limbs showing yet another alternative embodiment of clamping means;

FIG. 11a is a sectional view taken through the socket interface material in a portion of the joint of the structure of FIG. 11;

FIG. 16 is a perspective view of a socket interface arrangement for an upper leg amputee showing a two-limb prosthesis for the upper leg in accordance with the present invention which may be combined with the two-limb prosthesis for the lower leg and foot;

FIG. 17 is a side elevational view of a shoe or boot in which a brace structure similar to the prosthetic device of prior drawings has been incorporated and is shown in phantom;

FIG. 17a is a sectional view taken along line 17a—17a in FIG. 17;

FIG. 18 is a perspective view of a shoe similar to that of FIG. 17, but incorporating a slightly modified version of the structure shown in FIG. 17;

FIG. 19 is a side elevational view of still another modification of a structure for use in boots and shoes;

FIGS. 20a and 20b are perspective views of the structure of FIG. 19 disassembled;

FIG. 21 is a perspective view of a prosthesis of the general type shown in FIG. 18 but employed with a Symes socket for a lower leg amputee;

FIG. 22 is a partial perspective view showing a portion of a stump socket interface, a slot receptacle and a portion of a supported limb in a variation of the external slot receptacle of FIG. 9;

FIG. 23 is a sectional view taken along line 23—23 of FIG. 22;

FIG. 24 is a front elevational view of the structures of FIGS. 22 and 23 showing in phantom the canting capability of the structure.

FIGS. 25a–25e are schematic cross sectional views of various limb constructions showing laminate patterns in which the laminations are coiled;

FIGS. 26a–26j are views similar to FIGS. 25a–25e showing variations of layered laminations which may be used with the limbs of the present invention; and FIGS. 27a–27j represent similar views of coiled laminations around cores of various materials.

DETAILED DESCRIPTION OF THE INVENTION

Figure 1:
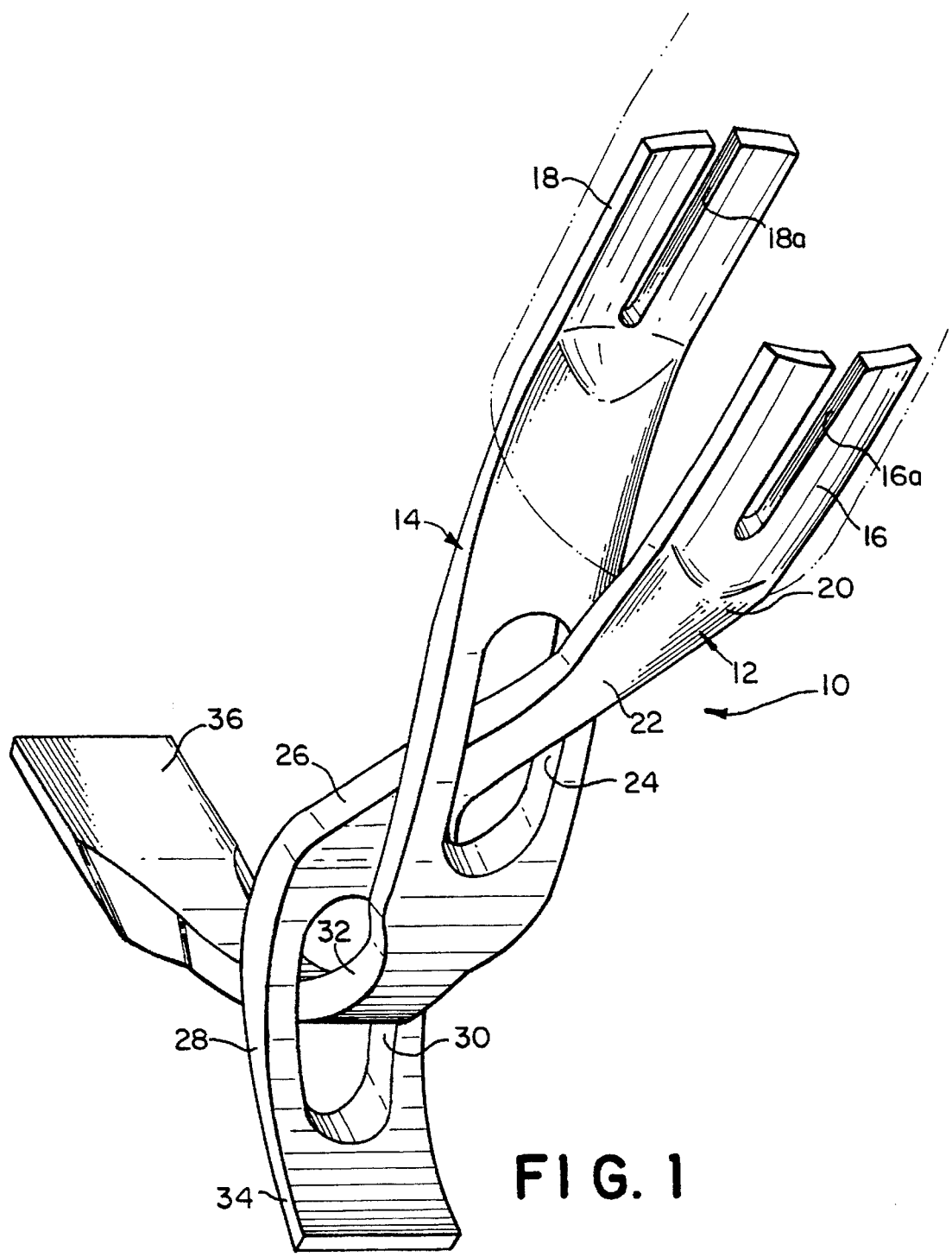
FIG. 1 is a perspective view of the principal limbs of a preferred embodiment of the present invention.

Referring first to FIG. 1, it will be seen that the prosthetic device generally designated 10 therein consists of two separate, but coordinated limbs 12 and 14. Limb 12 provides the heel portion and limb 14 the toe portion of the prosthetic device. As shown in FIG. 1, the limbs 12 and 14 are symmetrical about a center line drawn the length of the limb in each case. Each limb is composed of resilient spring-like materials, which may be a spring steel or an alloy selected for its spring properties or may be a composite (produced by Ciba, like R6264D High Modulus Prepreg Carton Fiber), filamentary or laminated material, such as snow skis are made of. Each limb has a relative rigid top shank 16, 18 which in many embodiments is curved to conform to a supporting member and which provides support of that limb from the mounting platform or supporting member, which in the case of an amputee is a stump socket interface, and ultimately from the stump of the amputee's leg. The prosthesis has been designed primarily for below the knee of the amputee, but can also be incorporated in a prosthesis for an above the knee amputee, as discussed below. The length, size and shape of each limb will depend to a large degree upon the elevation above the ground of its support. By supporting the limb at a higher point on the support, as socket interfaces and mounting platforms of the present invention permit, greater effective length of each limb may be achieved, essentially distributing the same stress over a larger area. The design of a particular prosthesis or brace, of course, is intended to be such that the prosthetic device as actually used will result in providing a simulated leg length corresponding to the actual leg length of the natural leg of the wearer. In many cases considerable modification will also need to be made to accommodate use under varying conditions and covers, shoes, and the like, which may account for variable length to the prosthesis as used, and therefore normally requiring some shortening of the length of both limbs or one limb from the point of attachment. For example, there may be a difference in toe and heel level due to shoes, which normally raises the heel somewhat above the toe. This may be exaggerated in the case, for example, of women's shoes with high heels. An adjustability of both of the individual limbs of the prosthesis relative to the support member and to one another is provided in order to be able to make a greater variety of compensations and is therefore a highly desirable and important feature of the present invention. Of course, a significant vertical adjustment ability also represents a potential longer useful life, as in the case of a youthful, growing amputee.

As seen in the embodiment of FIG. 1, and looking particularly at FIGS. 3a through 3g, the heel limb 12 has a relatively rigid support shank 16 curved out of the general plane of the limb, as seen in FIGS. 3c and 3d. The shank 16 is preferably provided with a lengthwise slot 16a running from the end of the limb for a predetermined distance. Otherwise, as seen in FIG. 3b, the shank preferably has edges uniformly spaced from one another and a uniform thickness sufficient to add to its relative rigidity. Below the shank, as seen in FIG. 2e, is a transition portion in which the limb 12 becomes flat across the cross section and starts to curve away from the general plane of the shank 16 and curve beneath the leg past the other limb 14.

Similarly, as seen in the embodiment of FIG. 1, and looking particularly at FIGS. 2a through 2h, the toe limb 14 has a relatively rigid support shank 18 curved out of the general plane of the limb, as seen in FIGS. 2c and 2d. The shank 18 is preferably provided with a lengthwise slot 18a running from the end of the limb for a predetermined distance. Otherwise, as seen in FIG. 2b, the shank preferably has edges uniformly spaced from one another and a uniform thickness sufficient to add to its relative rigidity. Below the shank is a transition portion in which the limb 14 starts to curve away from the general plane of the shank 18 and curves beneath the leg past the other limb 12.

Figure 5:
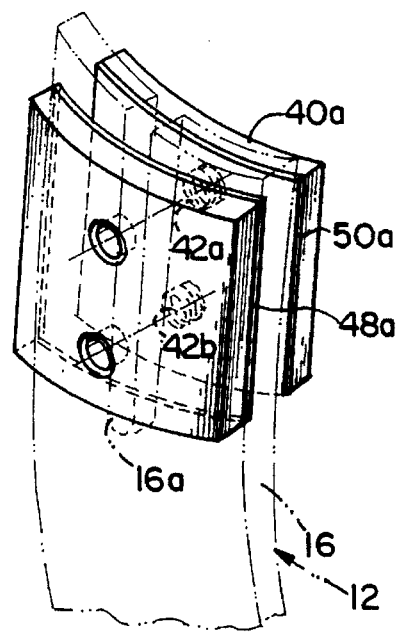
FIG. 5 is a partial view in perspective showing more of the detail of the construction of the clamping means employed in FIG. 4.
Figure 6:
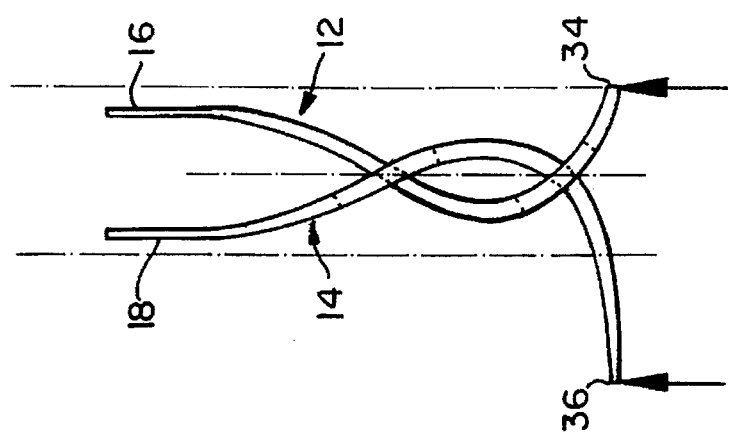
FIG. 6 is a side elevational view of the prosthetic device of FIG. 1 in rest or standing position.

The limbs 12 and 14 in this particular embodiment are designed to be considerably greater in width than the thickness. Each is somewhat diminished in width in a waist portion while increased in thickness. Specifically, waist portion 22 of limb 12, as seen in FIGS. 3b and 3f, narrows sufficiently to pass through an opening 24 in limb 14, best seen in FIGS. 2b and 2f. The width of limb 12 is preferably restored after the waist region 22 and its curvature is reversed in a region 26 into a much more sharply curved portion 28 through which is provided an opening 30, best seen in FIGS. 2b and 2g. Opening 30 accommodates a narrowed waist 32 of limb 14, which region is also subject to a reverse curvature of smaller radius than the opposite upper curvature. After the narrowed waist 32 of limb 14, which passes through opening 30, as best seen in FIG. 2a, the curvature diminishes and limb 14 terminates in a flat toe portion 36 which approaches a horizontal plane in the rest position of FIG. 6. Limb 12 also has a curvature back beneath the leg of the wearer, but in the waist portion 22 begins a sharper reverse curvature, as seen in FIG. 3a to the heel 34, which may be somewhat less horizontal than the toe 3b. The opening 30 in limb 12 is large enough to accommodate waist portion 32 without contact and to allow limb 12 sufficient clearance to be moved vertically up and down for heel position adjustment and at the position selected each limb 12 and 14 to operate independently of one another without contact. The reverse curve continues but diminishes in both limbs 12 and 14 so that both toe member 36 and heel member 34 are terminated in an almost horizontal orientation when the supported limb is supporting the weight of the wearer, but not walking, as seen in FIG. 5.

In the embodiment shown, the limbs 12 and 14 are fit together, for example by inserting shank 16 of limb 12 through the opening 24 of limb 14 and then placing the members in such orientation that the toe 36 may be passed through the opening 30 of limb 12. In order to do this, however, a small amount of torsion is ordinarily applied. The spring torsion ability built into the limbs 12 and 14 also adds to the life-like feel and terrain accommodation of the prosthesis.

Referring now to FIG. 2, one preferred means of attachment of the respective limbs to the stump of a lower leg amputee wearer is illustrated in FIG. 2.

Figure 8:
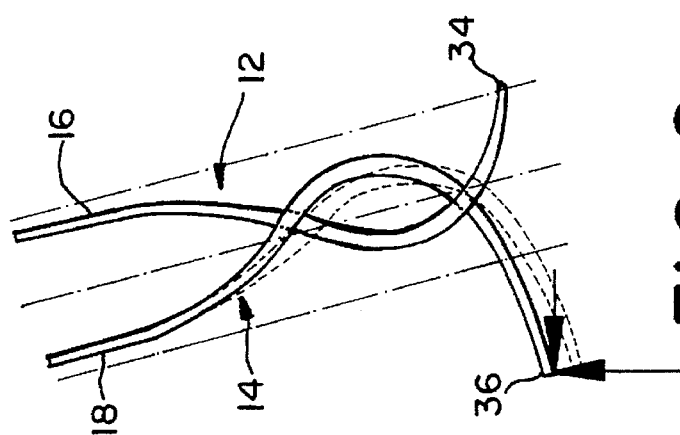
FIGS. 7 and 8, respectively, are similar side elevational views to FIG. 6 showing heel strike loading and toe strike loading, respectively.

Over the stump of the amputee's leg is first placed a thermoplastic liner 36 which is preferably molded and conforms to the shape of the stump. In accordance with the present invention, a new type of mounting platform is provided in the form of a molded rigid composite. For example, fiber and resinous material may be molded to form such a rigid composite mounting platform, which, in turn, is provided with integral limb attaching mounting blocks 40a and 40b, for example, of metal, or wood with metal inserts. An example of such mounting is shown in FIG. 8. The blocks are, in turn, rigidly molded into the composite mounting platform 38. To reduce weight of the platform, cutouts or openings 38a, 38b, 38c and 38d, for example, are provided. Additionally, there may be a slot 42 from the top edge 44 of the composite mounting platform. The rigid composite mounting platform or stump socket interface is preferably custom molded to the stump of the wearer, but by providing a slot 42 extending downward from the top edge 44, preferably in a somewhat diagonal or spiral manner, a range of adjustment may be provided to accommodate swelling or shrinking of the wearer's stump. Adjustment may be made by strap means 46, which may be molded into the body of the mounting platform 38 and have overlapping ends with a buckle or some other suitable means to accommodate adjustment, preferably infinite position adjustment. In addition suspension apertures 48a and 48b are provided on each side of the platform adjacent the top edge 44 to accommodate means such as straps or ties of various types which hold the platform 38 in place and prevent the platform and the prosthesis from being pulled or falling off the stump of the wearer.

The stump socket interface mounted receptacle itself may be made sufficiently strong to receive connector means to bolt the top shanks 16 and 18 of the limbs 12 and 14 in place. But, it will probably be desirable to include in the molded socket interface platform the mounting blocks 40a and 40b, which can be provided with openings threaded to receive bolts 44a or 44b. The bolts in the embodiment illustrated in FIG. 4 pass through holes in mounting plates 46a and 46b and through the grooves 16a and 18a, respectively, to engage the threaded holes 42a, for example, or corresponding holes for bolts 44b. The limb mounting clamp plate 46a or 46b conforms to the surface of the shank 16 or 18 and pulls the rigid shank into intimate rigid supporting contact with the socket interface. In practice, as seen in FIG. 5, it is often desirable to employ elastomeric sheet 48a and 50a on each side of the shank 16, for example, in order to provide some shock mounting for the limb, in this case limb 12.

Referring to FIGS. 2a through 2h and 3a through 3g, the shape and structure of each of the limbs 14 and 12, respectively, will be more clearly understood in their preferred form of this embodiment. From these drawings some comprehension of the relative size of the openings and the parts which have been narrowed to pass through them may be understood. It can also be seen that the limbs or pieces are designed to have broad flat surfaces which normally provide good stability against twisting, but can tolerate a small amount of twisting, such as required for assembly, and as may be necessary to accommodate uneven surfaces, for example.

As a practical matter, the two limbs as assembled and shown in FIG. 1, may then be held in place relative to one another by a band (not shown) temporarily affixed to the shanks 16 and 18 to hold them in place relative to one another for shipment or until actually connected to the rigid composite mounting platform. Once secured in place, the limbs 12 and 14 operate together in the sense that in a neutral position, such as that shown in FIG. 6, each contributes to support of the wearer. Limbs will be sized to generate responses during ambulation that correspond to plantarflexor energy absorption and energy return, as well as ankle moment of force cadences towards a goal of a conventional human gait, as described on pages 29–30 and 34–35 in "The Biomechanics and Motor Control of Human Gait", by David H. Winter, University of Waterloo Press, which publication is incorporated herein by reference. Obviously, a wide range of models and sizes will be required to replicate appropriate limb performance for the variety of amputee size, weight and activity levels.

It should be noted that the principle of indeterminacy, i.e., that many combinations of muscle forces can result in the same movement pattern, has been a guiding principle throughout the development of the present invention. Just as an amputee can adjust from one prosthesis to another in a short time, despite significant differences in performance of the prostheses, a new, higher level of energy storage/return capacity, as exemplified by the present invention, will enjoy the same adaptation feature, while, due to separate cantilevered heel and toe limbs in the case of a prosthesis, this invention offers a new level of adjustability, and accordingly a new ability to more accurately replicate natural human cadence.

Figure 7:
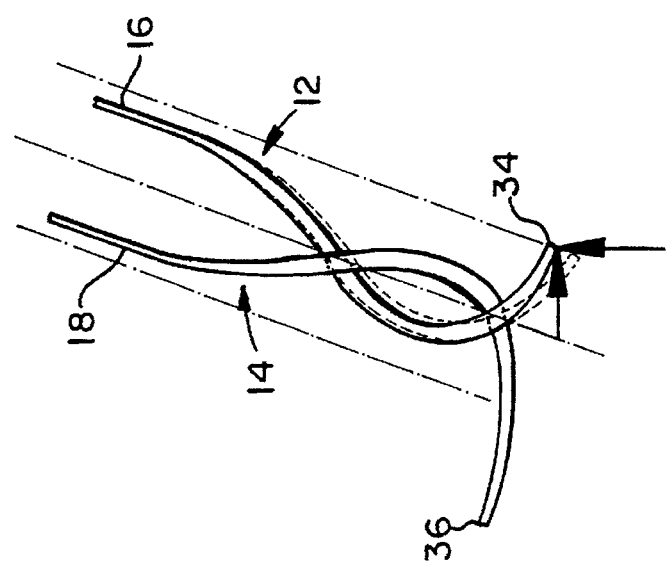

The force reaction becomes concentrated at the individual toe and heel pieces when a dynamic or walking mode is undertaken, as seen by the arrows in FIGS. 7 and 8 indicating reaction forces. In the heel strike position seen in FIG. 7, as weight is transferred to the heel, the heel is deflected from the dash line position to the full line position by considerably more force than the weight of the wearer, all of which force is shifted to the heel at that time. Maximum loading at the heel then diminishes as all of the weight is transferred to the toe, as seen in FIG. 8. Again, considerably more force than the individual's weight is then concentrated vertically at the toe.

Figures 9, 10:
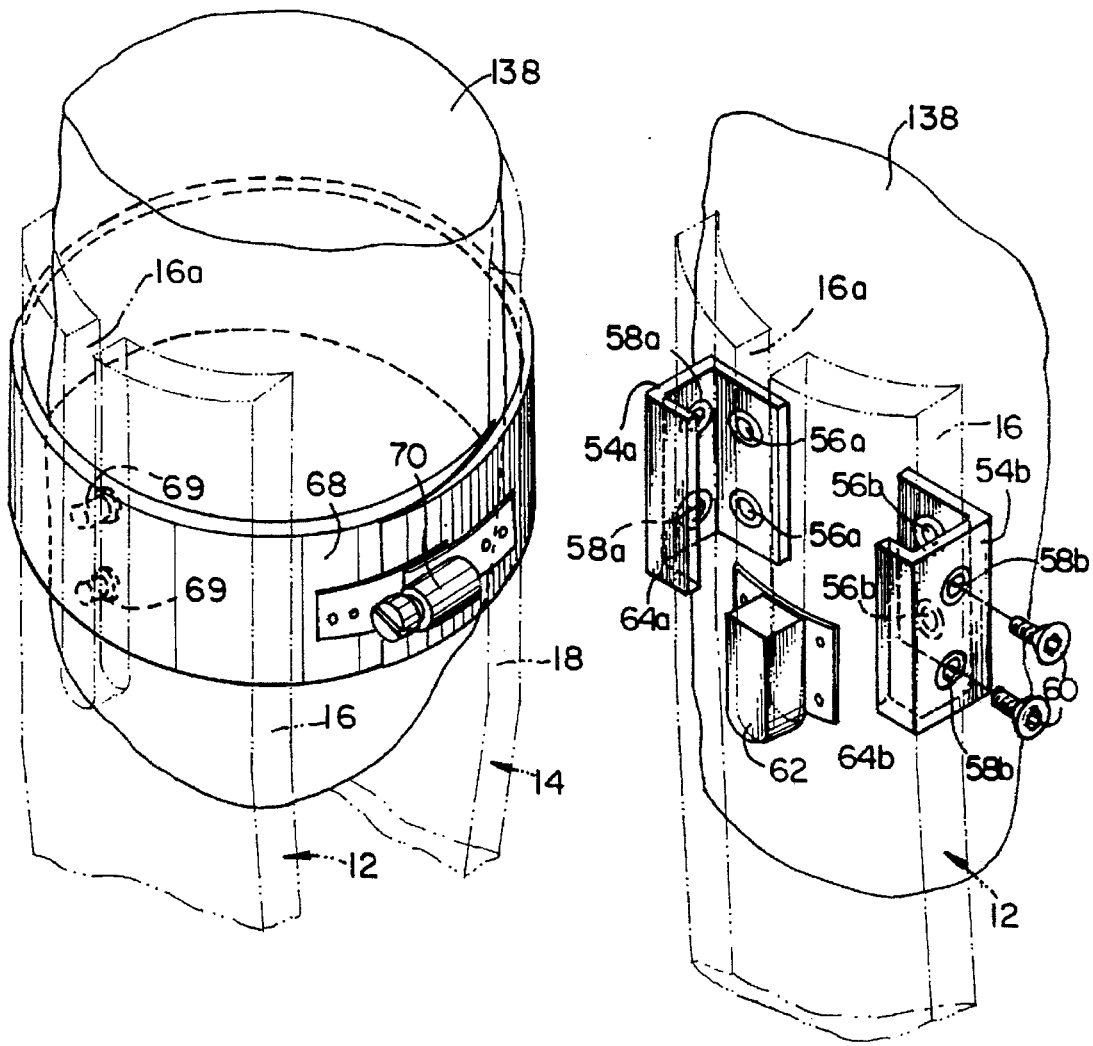
FIG. 9 is a partial perspective view which shows a portion of a socket interface having an alternative type of limb shank clamping means.
FIG. 10 is a perspective view of a socket interface attached to prosthetic limbs which employs yet another alternative embodiment of clamping means.

FIG. 9 is a view similar to FIG. 5 in which a pair of channel shaped brackets 54a and 54b are affixed to the rigid composite mounting platform to provide a slot receptacle for the rigid shank of the limb. The mounting is similar to that seen in FIG. 4 using screws 56a and 56b, respectively. The screws extend through openings in the sidewall of the channel shaped brackets to engage threaded apertures in metal plates molded, affixed, laminated, glued or pressure fit into the rigid composite or metal or laminate or plastic of the stump socket interface. The channel shaped brackets may be mounted directly facing one another to more easily receive a limb shank which is not curved as shown in FIG. 9, which shape is also easily accommodated usually with a somewhat looser fit. The brackets alternatively may be mounted on the curved surface of the socket interface to more easily accommodate a curved shank. In the embodiment shown in FIG. 9, threaded holes 58a and 58b accommodate screws which are received in the edges of the shank 16 of the limb 12. For example, threaded screws 60 engage threaded holes 58b. Preferably the channel members are arranged so that shank 16 is relatively received snugly within the channel members in a desired position and screws 60 may be brought into contact with the edges of the shank and tightened to hold the limb securely in place, preferably without making permanent screw holes in the shank. An elastomeric shock pad 62 may also be secured to the rigid composite stump socket interface to limit the upward movement of the limb by seating in the bottom of the groove 16a. The other outer channel sidewalls 64a and 64b are shown as shorter than the inner sidewalls and it will be understood that these walls could be equal in depth and even be more extended across the entire width of the shank to provide a one piece receptacle. The reason for avoiding screw holes in the shank is that such practice limits vertical adjustment of the limb to finite increments whereas with a structure in which bolts with flat ends press against an edge of the shank, continuous adjustment is possible just as it is with the construction of FIG. 4. An advantage of the construction of FIG. 9 is that it provides a low profile design less noticeable under a cosmetic cover for the prosthesis than in some other designs employing socket interface slot receptacle mounting.

FIG. 10 shows still another embodiment of support means for the prosthesis. In this case, the socket interface 138, providing a rigid composite mounting platform does not have to receive screws. It may provide adjustable locating pins 66 fitting into the slot 16a on the shank 16 of limb 12 and a corresponding alignment means for guide slot 18a of shank 18 of limb 14. In this case, however, the shank 16 and 18 are held in place against the socket interface 138 by a band or belt 68, which may be made of metal, leather or fabric, or any other suitable material. The belt or band 68 is wrapped around the shanks 16 and 18 of the limbs once they are in place. The ends of the band 68 are connected together by fastening the respective cooperating pieces of band clamp 70 which permit tightening the band 68 as much as desired by means of a universal adjustment, shown in FIG. 10 as a screw type adjustment. Various types of band clamps or buckles or other types of attachment means may be used, but types providing universal adjustment are preferred. The adjustable locating pins 66 may be provided in a track in the mounting platform, for example, and adjusted vertically to provide a stop contacting the bottom of the slots 16a and 16b, respectively. Preferably the locating pins are of a type easily adjustable by pushing or pulling a part of the pin to release the pin so that it can slide along the vertical track until positioned in a desired position by readjustment. A belt or band type arrangement of this sort can incorporate elastomeric shock absorption sheets both between the limb shanks 16 and 18 and the socket interface 138 and between the limb shanks and the band or belt 68.

If adjustability is not an important feature to the wearer, but permanence and stability is, the individual limbs may be permanently connected to the socket interface by gluing or laminating over or a combination of gluing and binding with belt or a wrap, like fiberglass, of material that may be impregnated with adhesive. Such treatment will have a physical appearance, at least in the preliminary stages, similar to FIG. 10 with the limb placement shown in phantom, but without the band 68, or with a different type of band or wrap to be secured by adhesive.

Figure 4:
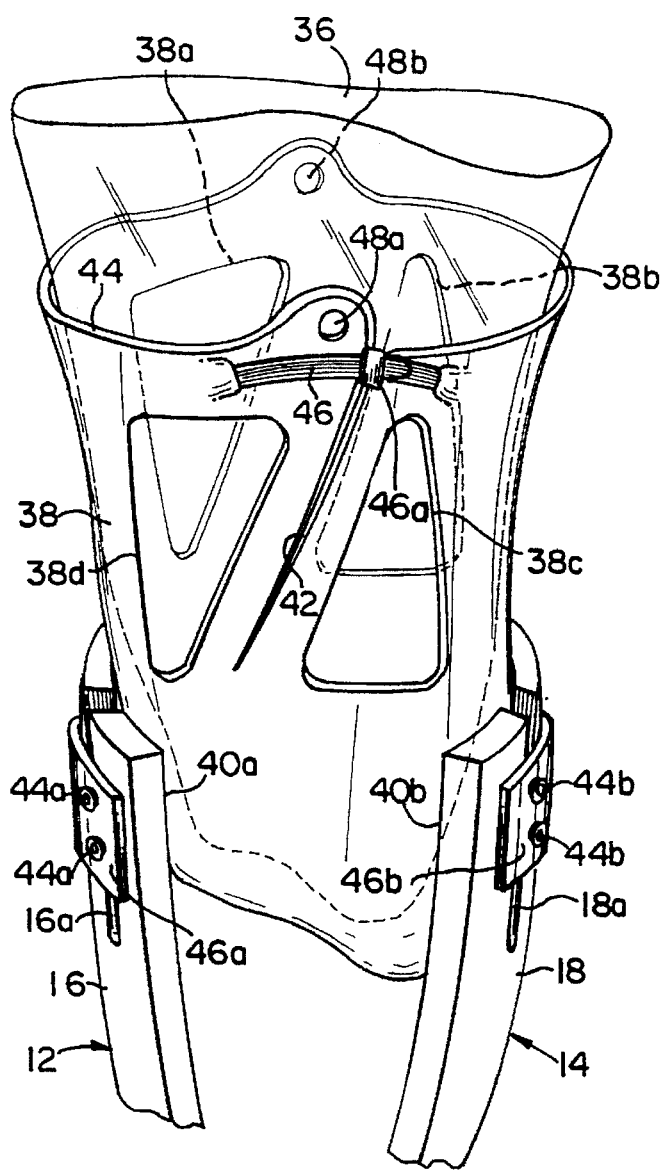
FIG. 4 is a perspective view showing part of the active portion of the prosthetic device of FIG. 1 and a socket interface used to attach the stump of the leg of an amputee to that active portion.

FIG. 11 employs a modified socket interface 138, which in many respects is like the socket interface 38 shown in FIG. 4. For example, it is molded to a custom fit to the wearer's stump. Like the structure shown in FIG. 4, the bottom portion, particularly in the region in which mounting blocks are imbedded, has its thickness increased for strength and rigidity. In this case, however, the socket interface is modified to include not just the mounting blocks, but the entire slot receptacle mounting structure which is shown in phantom in FIG. 11. In this case, the socket interface structure is sufficiently thickened to allow total inclusion of the channels 70 and 72, which respectively support the shanks 16 and 18 of the limbs 12 and 14. In this case, the molding process requires keeping the channels and, if they do not extend to the bottom of the socket interface, an aligned passage to each of the channels open from the bottom of the socket interface. Temporary plugs or any other removable means may be used in the molding process to keep the channels open so that they are free to receive the shanks 16 and 18 of the respective limbs. Alternatively, the channels could be cut out after the molding process. Bolts, such as Allen bolts 74 and 76, are introduced from opposite sides of the respective channel through the socket interface material and tapped holes in the sidewalls of the channels 70,72, respectively. As seen in FIG. 11a, the bolts are angled inwardly instead of being brought in normal to the channel sidewalls, primarily as a means of reducing the length of the bolts 74 and 76 and to minimize the amount of drilling and tapping through the socket interface that needs to be done as well as to keep actual socket interface thickness, and thus weight, to a minimum. At least one additional bolt 78,80 is provided near the top of each of the respective channels to abut the end of the shanks 16,18. Bolts 78 and 80 can be used as stops to determine how far into the socket interface the shank will be allowed to extend and as a preliminary adjustment in fitting the limbs. Repositioning of the screw can account for over one inch of vertical adjustment if desired. In some cases, screws of various length might be used to accomplish the different levels of adjustment desired. Once the shank is in position, the screws 74,76 are tightened from both sides to hold the limbs 12 and 14 firmly in position as shown in FIG. 11a. If desired, some clearance may be provided laterally in the channels in order to afford the opportunity to provide a few degrees of outward adjustment, or canting, depending on, and possibly permitting matching of, the natural stance of the other leg of an individual wearing a prosthesis.

It will be observed that in this case the shank has been made straight. It is, of course, desirable to minimize the size and weight of the socket interface, in which event the shank is curved, as shown in other embodiments. Of course, the channel for receiving the curved shank is preferably appropriately curved, as well as providing an overall curvature to the whole slot receptacle in which the curved shank is received.

Figure 12:
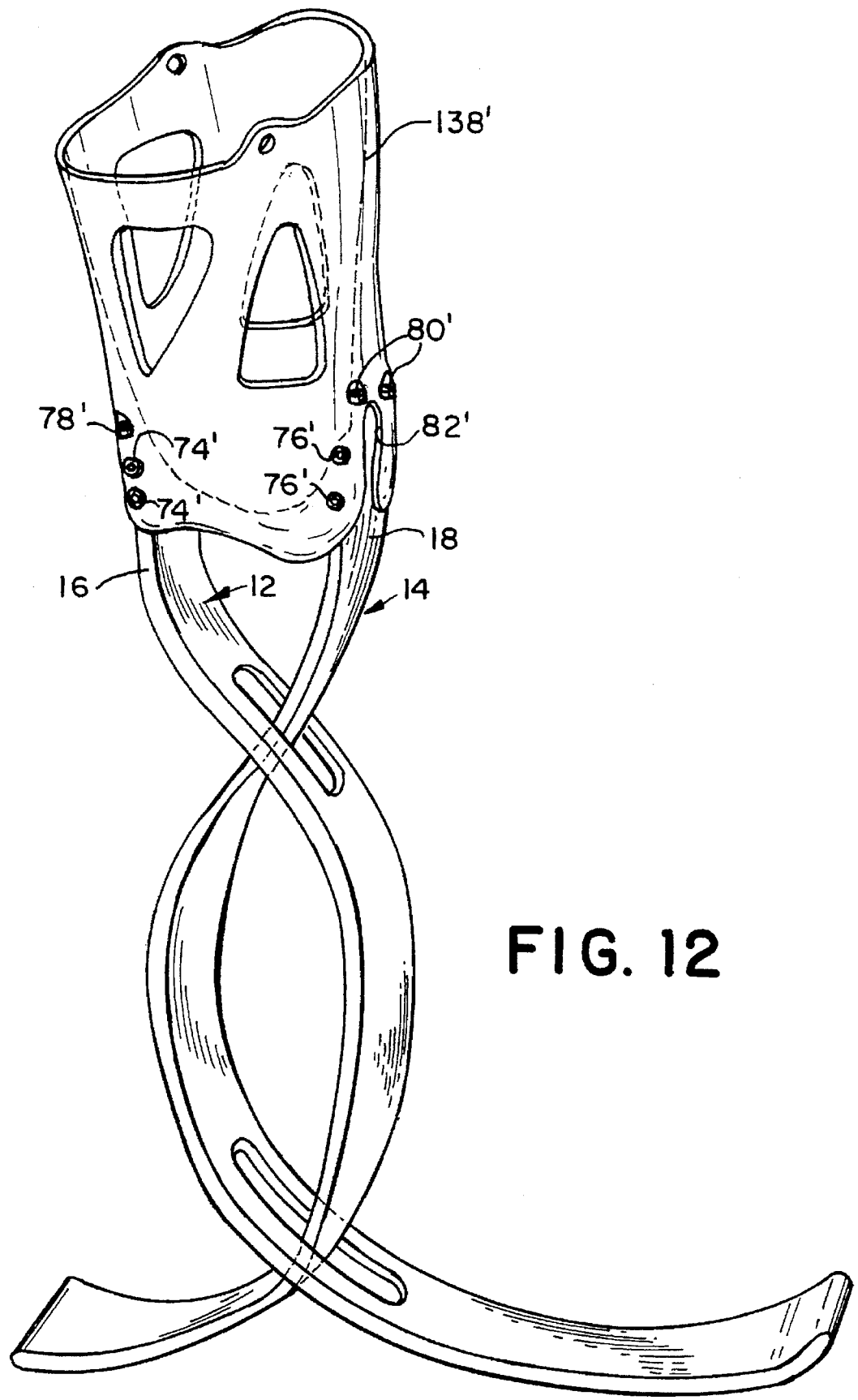
FIG. 12 is another perspective view similar to FIG. 11 in which an alternative socket interface provides another variation on the structure of FIG. 11.

Referring now to FIG. 12, a variation on the socket interface of FIG. 11 is shown. In this case the slot receptacles for receiving limb shanks are not completely embedded in the molded stump socket interface, but a viewing channel laterally into the slot receptacle is provided by lateral opening 82 into the slot. This opening also allows reduction in the amount of material molded into the socket interface, providing a reduction in weight. The lateral opening 82 allows observation of the positioning of the shank in the course of fitting. The use of materials capable of being threaded and maintaining the threads for the socket interface enables the metal channel 70, as seen in FIGS. 11 and 11a, to be omitted where threads through the molded material of the socket interface are sufficiently strong to hold the bolts in position. Here the socket interface is designated 138' to indicate it is similar to that of FIG. 11, but with small differences. Screws 74' and 76' are employed in the same way to hold the shank 16,18 of the limbs 12,14 in position. In this case, however, two screws 78' and 80', respectively, are used at the top, not only to act as stops, but to hold the shank more firmly in a selected position, particularly when the canting feature is desired. In such event, the slot for the shank provides a relatively loose fit so that the shank may be rocked slightly from side to side within the slot. The slot is still intended to have relatively close tolerances so that with the final positioning of the limbs 12,14, the screws 74', 78', 76' or 80' may be tightened down in firm contact with the surface of each shank after it has been moved to its final functioning position, holding the limb in a precise predetermined position. The use of two bolts at the top against the top edge of the shank, and two bolts on each side of the shank, the final positioning of the shank and its supported limb is very stable. It will be understood that the bolts do not enter the face of the shank against which they bear. In order to further protect the surface contacted by bolts against damage, a coating or plating, preferably metallic, is provided of sufficient thickness and hardness to withstand the forces imposed on the shank edges and ends by the bolts in the course of use of the prosthesis. This construction considerably reduces weight, particularly of prosthetic limbs made of snow ski construction. The construction of FIG. 12 is preferred in that it provides a very simple construction and still allows for vertical adjustment, as well as canting of the limbs toward the outside at the bottom to a limited degree to achieve balance with the other leg. In addition, as with all embodiments, the center of gravity of the leg is raised relative to conventional lower limb prosthesis. It will be understood that the screws used are intended to provide a small contact area which gives a maximum adjustability, but once the screws are all tightened after the position of the limb is selected, the limb will be held very firmly in position even during heavy use.

Figure 13:
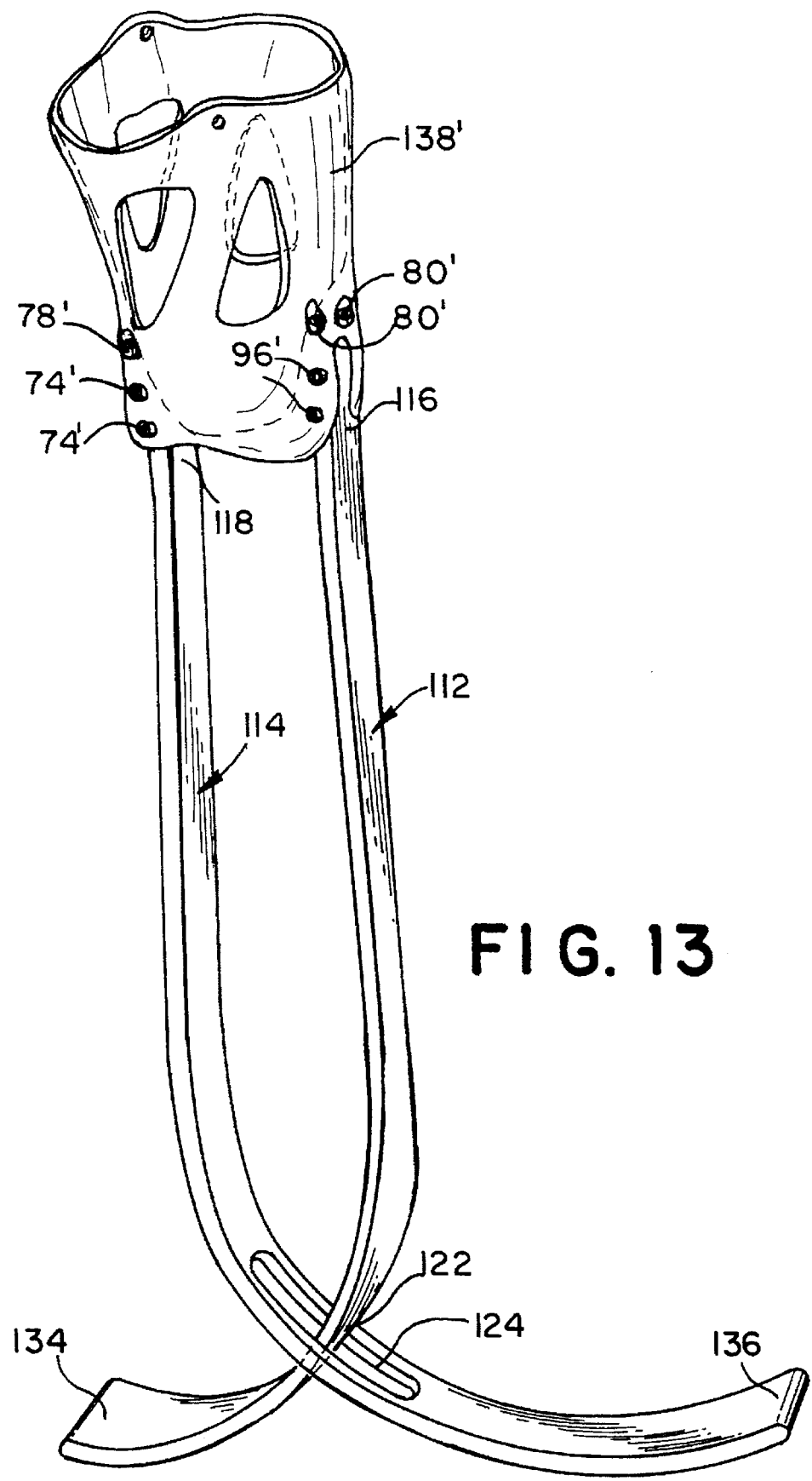
FIG. 13 is a perspective view similar to FIG. 12 showing an alternative form of a prosthesis in which one limb passes through the other at only a single place.

FIG. 13 shows a socket interface of the type shown in FIG. 12 having limbs of a different configuration such that they pass through each other only once. In the configuration shown, the limb 112 providing the heel portion 134, is the one which is provided with a narrow portion 122 which passes through opening 124 in limb 114. Again, in this structure, as in that of FIG. 12, the slot receptacles provide sufficient clearance for the shanks 116,118 of the respective limbs 112,114 to allow Allen bolt adjustment to set and hold any selected orientation and height adjustment within the limited range of movement of the shank within the slot receptacle. This might be up to several inches in height adjustment and a limited angular movement, say on the order of 7 degrees laterally, outward from the bracket. The use of separate limbs and separate accepter brackets allows the limbs to be individually adjusted as to height, although presumably one would wish them to be correspondingly adjusted as to lateral angles. Once the bolts have been set the position will be maintained with great stability until the decision is made to readjust. Loosening the bolts will permit height adjustment or angular realignment and then retightening the bolts will secure a very stable solid support for the limb involved.

FIG. 13 also provides an arrangement whereby it is possible for the device to be adapted for an above the knee amputee in a case where the knee joint is ignored. As mentioned below, the present invention accommodates use of artificial knee joints as well.

Figure 14:
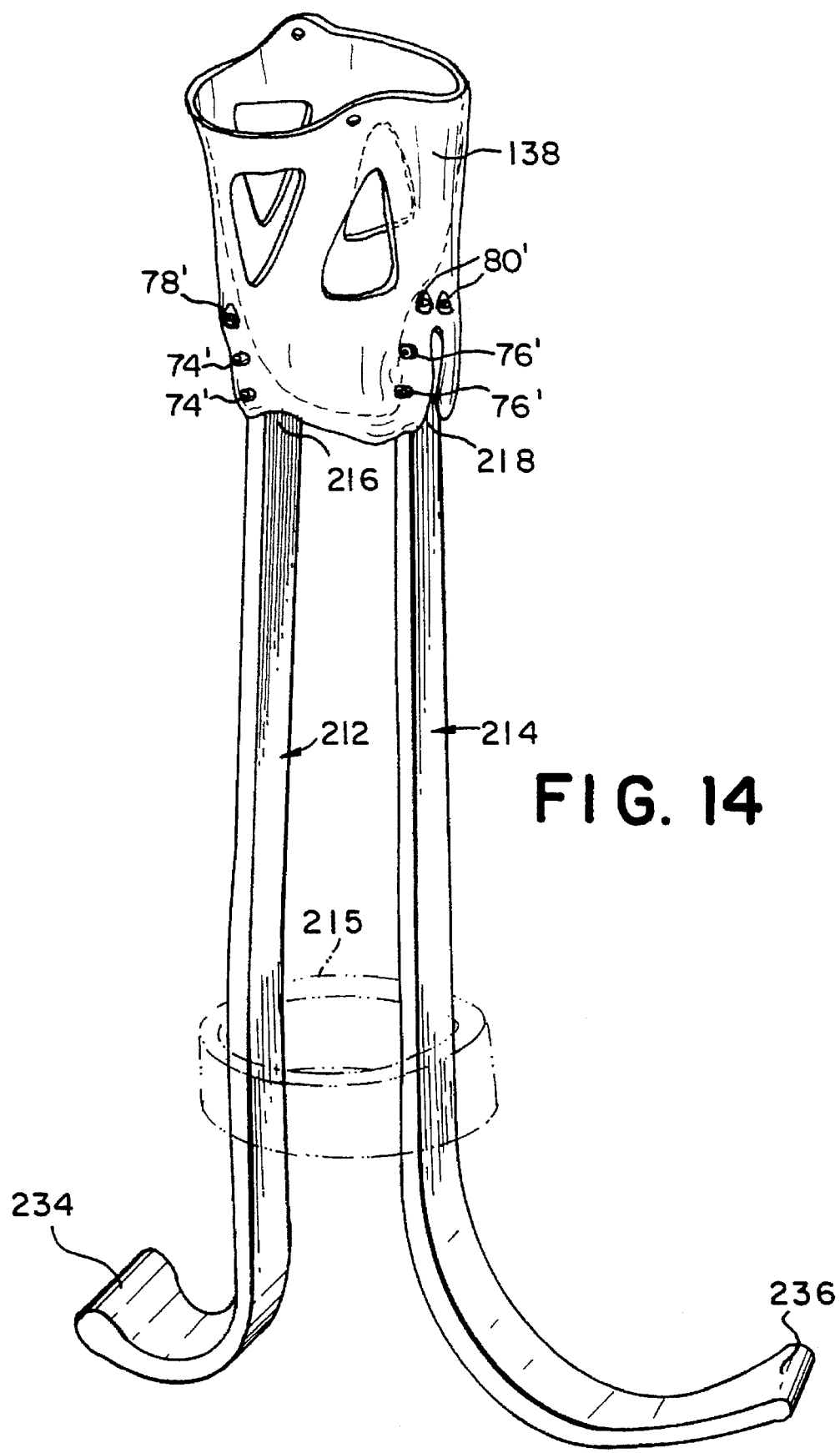
FIG. 14 is a perspective view similar to FIG. 12 showing still another alternative form of a prosthesis in which the limbs do not pass through each other at all.

FIG. 14 shows a construction in which there is no pass-through of the respective limbs 212 and 214. In this case, the limbs 212 and 214 providing heel portion 234 and toe portion 236, respectively, are shown relatively straight over much of the respective lengths, but it will be understood that either, or both, of them may have additional curvature built in for a designed spring effect. It is anticipated that it may be desirable and necessary to provide a restraining structure 215, shown here as a ring. The restraining structure could easily be any other type of structure which effectively provides a stop to limit the outward spread of limbs 212 and 214 away from one another. The ring 215, or other restraining structure, most conveniently is supported on one limb with the other limb, of course, detached and spaced from the ring. The position of the stop and its method of support is a matter of individual design and will depend upon the design of the individual limbs 212 and 214. It will be observed that the structure of FIG. 13 with the single pass-through provides its own limiting stop in terms of the ends of the opening 124.

In other respects, the socket interface 128 may be the same as the socket interface of FIGS. 12 and 13 having lateral bolts 74' and 76' to engage the respective side edges of limbs 212 and 214 and bolts 78' and 80' to provide limiting surface to the top edge.

It will be observed by those skilled in the art that the type of slot receptacles employed to receive limbs shown in drawings before FIG. 11 is desirable, particularly because it provides external mounting where ease in view adjustment is important, but mounting internally within the molded material of the socket interface itself may often be cosmetically most easily covered.

Figure 15:
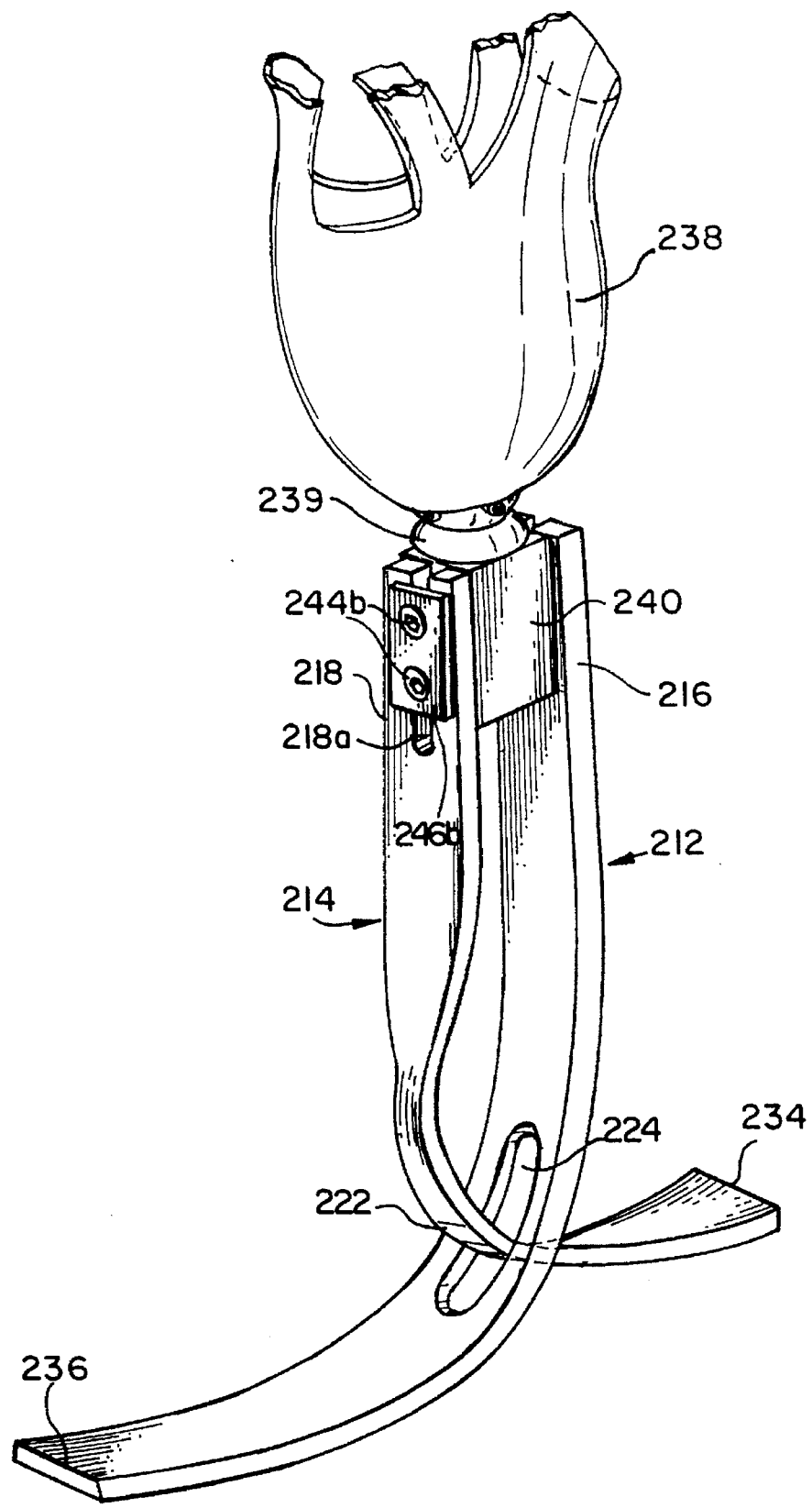
FIG. 15 is a perspective view of a prosthesis in accordance with the present invention attached to a conventional prior art socket interface, modified for use with the present invention.

Referring now to FIG. 15, a conventional socket interface 238 widely used today by amputees is represented. Such a socket interface uses what is frequently referred to as pyramid interface 239, which may be composed of aluminum, titanium, steel, graphite or a high modulus epoxy material. In this case, the pyramid interface is connected to a rigid mounting block 240. Such a mounting block easily provides opposed flat faces to which flat shanks 216 and 218 may be mounted to support limbs 212 and 214, respectively. The limbs as shown here are a single limb pass-through wherein limb 214 is narrowed at 222 to pass through opening 224 and limb 212. Limb 214 provides heel portion 234, whereas limb 212 provides toe portion 236. Clamp plates of which plate 246b is representative may be used and clamped to the block 240 by countersunk Allen bolts 244b passing through a vertical slot 218 to hold the limb 214 to the block 240. Similar structure, of course, exists on the opposite side of the block to hold limb 212 to the block structure.

FIG. 15 simply illustrates that the present invention in all of its forms can be used with the conventional type socket interface. Thus, any of the shapes illustrated, or any of the shapes possible in accordance with the invention, can be used. Also the shanks may be cylindrically or otherwise curved to conform to similar curvature of the block from which they are supported, if desired.

FIG. 16 illustrates a different situation where only a partial prosthesis for an upper leg amputee is shown. Here a socket interface 338, which may be made in accordance with the present invention, molded to the amputee's stump, is provided on the upper leg above the knee. FIG. 16 illustrates only the upper leg portion to which is attached at the mounting bar 302 a conventional prosthetic knee joint (not shown), such as, for example, the Stabilized Pyramid Knee, produced by Hosmer Dorrance Corporation of Campbell, Calif. Such a knee structure will allow the prosthetic leg to bend at the prosthetic knee structure provided. As in the lower leg prosthesis, a pair of limbs 313 and 315 are provided and arranged generally in a front to rear configuration. The limbs may be structures of a type employed for the lower leg prosthesis and may have a bypass or pass-through construction employing any of the material and techniques discussed above. The limbs 313 and 315 have shanks 317 and 319, respectively, which are received within accepter brackets similar to those of FIGS. 12 through 15, wherein a set of six Allen bolts 374 and 378 bear against the respective side and end of the shank 317 and Allen bolts 376 and 380 bear against, respectively, the sides and ends of shank 319. This type of construction is used instead of heel and toe portions. The otherwise free ends of limbs 313 and 315 are each attached to a knee connection member 302 to which as mentioned above is attached the knee. The knee, in turn, is attached below the knee, for example, to a structure like the one shown in FIG. 15, or a variation thereon which would be obvious from other disclosure herein. The knee could also be attached to any other known suitable leg and foot prosthesis.

In constructing a prosthesis for an above the knee amputee, inclusion of a knee joint is desirable, but also adds considerable complication to the structure. In addition, the spring effects of the upper and lower leg prosthesis must be matched so that they will reinforce and not diminish one another.

From the description of modification of the prosthesis to provide a brace, it will be understood by those skilled in the art that a prosthesis itself need not be in the symmetrical form shown in FIG. 1, but might employ side by side limbs of substantially modified form from limbs 12 and 14 in FIG. 1. A principal advantage of the limbs of FIG. 1 is their symmetry which permit the limbs to be individual and yet effectively pass one another without one interfering with the operation of the other. Thus they provide a symmetrical distribution of vertical force or components of force.

FIGS. 17–20 show side and perspective views of a brace adaptation of the prosthetic device of the present invention. In these FIGS. various brace structures for use in shoes, boots and other footwear are shown. It will be understood that in such embodiments the mounting platform is the shoe or boot. Where a brace is used outside a shoe or boot, the shoe or boot may still be used as the mounting platform or the brace may be attached to the leg by some other common band, or the like, which provides a common support for the shanks of the limbs at the upper end of each limb. Advantageously each of these braces consists of two pairs of limbs or members similar in profile to the shapes as seen in FIGS. 2a and 3a. The limbs or members in some cases are separate and in others are connected together at the toe and heel, respectively.

More specifically, FIG. 17 shows a shoe 92 to be worn on the foot of a person having a normal or a somewhat impaired foot in which a brace in accordance with the present invention is employed. Like the prosthesis, the brace consists of individual limbs 412a and 414a which in profile look similar to the limbs of FIGS. 3a and 2a, respectively, when viewed in the side elevation of FIG. 17. In this embodiment there is a second set of similar limbs 412b and 414b (not shown) on the opposite side of the shoe. One pair of the limbs 412a and 414a pass within or along the right side of shoe 92 and the right side of the wearer's leg or foot. The second pair 412b and 414b pass on the left side of the leg along the left side of the shoe. In the shoe brace version the importance of keeping the width of a prosthesis wide disappears because the leg and foot contribute to stability. Various forms of limbs are possible, but a preferred one, as see in FIG. 17a, is a spring steel core covered by a composite fibre or graphite oval tubular cover having its long axis directed front and back and its short axis directed laterally. Such limb construction permits a relatively flatter structure which is also quite amenable to forming and deforming into patterns conforming to the shape of a shoe or boot, for instance. Also, this configuration eliminates any need for one limb to pass through the other. Instead, they lie side-by-side with no deviation or cutting away of either limb required. The shank 416a and 418b of each limb is anchored securely at its top to a band 417, which conforms to the shoe and may even be a part of the shoe. The shanks 416a,418a (and 416b,418b on the other side) are engaged or even molded into the flexible band 417. Band 417 may be double stitch sewed to the shoe around the top in proper orientation to hold the respective limbs 412a and 414a of the brace in proper position relative to the shoe 92 and the sides of the leg. At the bottom of the shoe rigid holders 433a and 435a permanently secured to the shoe 92 are provided in out of the way recesses to engage and secure the heel end 434a and the toe end 436a, respectively, in place. Corresponding holders 433b and 435b are provided on the other side of the shoe to hold heel and toe ends of limbs 412a and 414a, respectively, in place.

In addition to being built into shoes and boots, similar structures to those of FIGS. 17–20 and for that matter modifications of other structures described, may provide braces outside of shoes or boots where the need dictates such use. In addition to providing bracing, the structure of FIG. 17 and similar structure have non-prosthetic applications used in combination with shoes or boots for use by hikers and athletes to give increased resilience to their walking and running and increased height to leaps by efficient use of energy stored in the resilient limbs, as well as damping shock experienced by foot and ankle.

FIG. 18 shows a modified boot or shoe 92 having a pair of limbs 412 and 414 similar in most respects to those of FIG. 17. As seen in the further modified limb structures shown in FIGS. 19, 20a and 20b, limb 414" provided with toe connection portion 436' and limb 412" is provided with heel connection portion 434'. The shank termination 416a', 418a', 416b' and 418b' are all secured to the reinforced band 417' at the top of the shoe or boot. The boot is capable of being opened in front for easier insertion of the foot of the wearer and is provided with clamp members 421 attached to the boot at opposite sides of the opening. Clamping member 421 allows the boot to be closed by attaching the portions and preferably allows the boot to be pulled tight, by a toggle arrangement, or similar device, as with ski boot buckles. A slightly modified structure similar to FIG. 18 more clearly shows limb structure in FIGS. 19, 20a and 20b. Variations such as the interconnection of the limbs 412' and 414', shown in FIGS. 19, 20a and 20b, require slots 411a, 411b and 413a and 413b through and extending along the limbs, which, in turn, receive coupling pins 415a and 415b and 419a and 419b, respectively, which slide along the slots. The pins 415a and 415b and 419a and 419b are more in the nature of rivets which effectively tend to hold together the adjacent portions of the limbs 412a' and 414a', for example, and control their movements relative to one another. The shank ends 416a" and 418a" are held in modified pockets 422a and 424a, respectively, which may be made of Kevlar® double stitched to the reinforced band at the top of the shoe or boot.

FIG. 21 shows a somewhat hybrid construction in which limb structures similar to those of FIGS. 17–20b are used as a prosthesis for an amputee whose lower leg extends down to the vicinity of the ankle area. Such an amputee may employ a Symes socket 538 which may be longer and extend further along the leg above the stump than other stump socket interface structures shown heretofore. Because the Symes socket extends so high, it is possible to take advantage of the socket and mount the two shanks 516 of limb arms 512a and 512b at a much higher position well above the distal end of the socket, thereby allowing the amputee the better feel of a higher mounting. Limbs 518a and 516a may be secured to the Symes socket by a band 517. Limbs 512a and 512b are connected by the heel piece 534 and limbs 514a and 514b are connected by the toe connection 536. The use of the boot 594 thus provides both the function of helping contain and hold in place the prosthetic limbs and the function of providing a cosmetic cover for the prosthesis.

Referring now to FIGS. 22, 23 and 24, the structure shown is intended to represent the type of slot receptacle in which a slotted shank of the limb is snugly received. The molded stump socket interface 638, a portion of which is shown, will be understood to be similar to socket interfaces previously described. Fixed to the socket interface is a plate 617 which may be molded in place, put in place with screws or otherwise attached so that it cannot move. Plate 617 has a surface 617a projecting beyond the surface of the socket interface that is knurled. A cylindrical shaft 620 projects through plate 617 and is preferably molded in place so that it cannot rotate and may be provided with a head which abuts the back of plate 617. The end of the shaft 620a is threaded to receive the internally threaded knob 625. The slot receptacle 664 is preferably an extruded channel member having flanges 664c, partially enclosing the shank. Plate 617 is provided with the appropriate shape to conform to the bottom of slot receptacle channel 664. A hole through the bottom of the channel allows shaft 620 to pass. The channel is then free to rotate about shaft 620 as seen in FIG. 24 since the channel is not elsewhere attached. However, the back surface 664a, which opposes surface 617a of the plate is preferably knurled so that when these surfaces are held together by spring force they will resist relative rotation. Alternatively, high friction material may be secured to the surface plate 617 to prevent relative rotation, or other known techniques may be used. The inside bottom 664b of the slot receptacle is also knurled. Limb shank 616 of limb 612 is provided with a longitudinal shank slot 616a from the end of the shank which allows the shank to pass the shaft 620 as it is inserted into the slot receptacle 664. The shank is preferably relatively close fitting at its edges, but loose fitting between the bottom and the flanges 664. Within that space around shaft 620 and inside the slot receptacle flanges 664c is a flat washer 621 against which presses a Bellville washer 623. Knob 625 holds washer 623 in place and compresses against flat washer 621 and, in turn, against shank 616. When the knob is removed or moved outward from the socket interface to a point where the spring 623 is not compressed, it will begin to release the pressure from washer 621 and, in turn, the pressure against the shank 616 allowing the shank to be moved up or down within the slot receptacle for height adjustment of the limb. Relief of the pressure of washer 623 also allows the slot receptacle channel 664 to be moved away from plates 617 so that the knurled faces 617a and 664a can be separated and the slot receptacle can be turned relative to the faces as seen in FIG. 24. This allows adjustment of the cant and rotation angle of the limb 612, but once the knob is screwed down against the Bellville washer 623 the pressure returns and the receptacle stays in its new rotated position relative to the plate 617. Likewise, the pressure through the washer 621 causes the limb shank 616 to be pressed against the knurling 664b and held in place against movement up or down. The knob 625 is preferably made with a very low flat profile, but with finger holes as shown to allow the knob to be rotated and thus moved in or out on the threaded end of shaft 620 to apply or relieve pressure.

Referring now to FIGS. 25a–25e, the structures shown are schematic representations of lamination patterns that may be used in connection with the limbs of the present invention where the laminate is the sole member used for the limb. A preferred material for the laminate is carbon fiber. Other suitable materials may be substituted. The variations shown are not meant to be limitations, but merely examples of ways in which coiled laminate structures may be made for use as limbs according to the present invention.

FIGS. 26a–26j are schematic representations showing patterns of laminae which are layered rather than coiled. Again, it will be understood that these represent some shapes and some patterns of lamination, but many others are possible.

FIGS. 27a–27j all represent core lamination. FIGS. 27a–27e represent coiled laminations over center cores. FIGS. 27f–27j represent layered laminations over center cores. The core may be spring steel as in the FIG. 17a construction or it may be other metal, including alloys of various types usually selected for their spring property, or plastics, rubbers, foams, woods and many other possible materials. The laminations are also of various types of materials. Again, material mentioned earlier in the specification is preferred for its properties, but many types of materials may be used. Where no core is employed, the resilience of the structure depends upon properties of the laminate materials. Otherwise, resilience may be supplied from the core only or from a combination of the core and the laminate. If supplied by the core only, the laminate still must have properties which allow elastic stretching. In some cases, the adhesives are a variation of the lamination material. More often, they are well known resins used for adhesives by many manufacturers.

In addition to variations in the form of limbs shown for prosthesis in accordance with the present invention, many other variations and modifications will occur to those skilled in the art. The same is true of socket interfaces, mounts and connections disclosed herein. Many variations are possible and will occur to those skilled in the art. All such modifications and variations within the scope of the claims are intended to be within the scope and spirit of the present invention.

I claim:

1. A spring limb support device simulating or supplementing the feel and action during walking of a human foot and lower leg comprising:

a mounting platform for providing connection to the leg of a human wearer;

a pair of monolithic independent limbs, each of which simulates a part of the leg, independently extending to the mounting platform, part of one of which limbs simulates the toe and front part of the foot and part of the other of which simulates the heel of the foot, each of said limbs being composed of resilient spring material and being curved to deform under the weight and dynamic forces of body movement and each being separately cantilever supported on the mounting platform by a terminating support shank such that separate height adjustment of each limb may be made independent of the other limb, the shanks of the respective limbs being spaced from one another when worn so that the respective foot portions cause each limb to respond independently to forces from the ground and react with different separated portions of the mounting platform with a feel to the wearer like that of a normal foot and leg.

2. The spring limb support device of claim 1 in which each of the respective limbs has a curvature in at least one direction away from alignment with the shank.

3. The spring limb support device of claim 2 in which the curvature of each limb causes the limbs to cross paths at least once.

4. The spring limb support device of claim 3 in which the curvature of each limb is compound and causes the limbs to cross paths at least once.

5. The spring limb support device of claim 4 in which each limb curves toward the other from the supported shank of each, passes the other and curves back toward the other and past its supported shank prior to termination in toe and heel portion, respectively.

6. The spring limb support device of claim 5 in which the limbs are single members extending from shank to toe or heel and the toe and front part of the foot and the heel of the foot are aligned with one another as are the shanks of the limbs and arranged so that portions of the limbs must be cut away in two regions to allow the limbs to pass one another.

7. The spring limb support device of claim 5 in which the limbs are cut away so that they may pass one another by providing a hole in one member and a narrow waist in the other at the positions where the limbs pass whereby the limbs are interfitted to have one limb pass through the hole in the other in two locations.

8. The spring limb support device of claim 7 in which the holes are made sufficiently large to permit movement of one limb relative to the other as well as to permit vertical adjustment of one limb relative to the other at the mounting platform which is a stump socket without interference between the limbs.

9. The spring limb support device of claim 2 in which the limbs do not cross each other's paths but a stop member is provided on one extending past and into the path of potential movement of the other.

10. The spring limb support device of claim 1 in which the mounting platform is a composite stump socket, which socket has included as an integral part of the structure spaced apart slot receptacles to receive the respective shanks and fasteners by which the limbs are held in a selected position within the slot receptacles.

11. The spring limb support device of claim 10 in which the stump socket provides attachment means for the slot receptacle for the shank of each limb to the stump socket and means providing the slot receptacles are attached to the stump socket by attachment means, and fasteners engaging the shank of the limbs and the slot receptacles are provided to hold the respective limbs in place on the socket interface.

12. The spring limb support device of claim 11 in which the shanks of the limbs received in the slot receptacles have shank slots extending the direction of relative movement permitted the shanks in the slot receptacles and fasteners extending through the shank slot and engaging the stump socket are engaged by and hold clamp means against the shank to secure the limbs and prevent movement of the limb relative to the stump socket.

13. The spring limb support device of claim 11 in which the limb shanks employ shank slots into the ends of each limb extending generally lengthwise of the shank in the general direction of insertion of the shank into the slot receptacle and attachment means including a conforming adjustable limb mounting plate placed against the shank opposite the stump socket and screw means passing through the plate and engaging the mounting block, whereby when the screw means is pulled snugly into place the limb is rigidly supported but such that the screws may be loosened and the limb adjusted vertically through an infinite number of positions limited only by the length of the shank slot and the shank slot receptacle.

14. The spring limb support device of claim 10 in which the stump socket is connected to the respective shanks by suitable fasteners bracket means which provide slot receptacles for the shank of each of the limbs, and further fastening means engageable between the bracket means and the limb is provided to hold the limb in a selected position relative to the stump socket.

15. The spring limb support device of claim 10 in which the limbs are each provided with a shank slot extending from the end into the shank in the general direction of the slot receptacle, and shock absorbent means supported and positioned on the stump socket interface in position to engage the bottom of the shank slot.

16. The spring limb support device of claim 10 in which the slot receptacle is a unitary channel member which is so attached to the stump socket that it can be rotated relative thereto to permit canting of the limb, the shank of which is received in the channel member.

17. The spring limb support device of claim 16 in which the channel member has a non-slip surface which cooperates with a non-slip surface of a plate fixed to the stump socket so that the channel member is rotated relative to the plate in canting a limb; but provides a non-slip interface between the channel member and the plate in whatever angular position the two surfaces are clamped together.

18. The spring limb support device of claim 17 in which the channel member is rotatable relative to a shaft fixed relative to the stump socket interface about which it is rotated in canting adjustment and clamp means used to hold the limb shank in place also holds the channel member to the plate, whereby release permits both adjustment of cant and height adjustment of the limb.

19. The spring limb support device of claim 18 in which the clamp incorporates a dial knob easily manipulated by hand permitting sufficient release of the clamp from the limb for height adjustment.

20. The spring limb support device of claim 10 in which the slot receptacles provide spring clamp means to hold the limbs in place in the receptacles, means is provided to release the clamp so that the limb may be height adjusted.

21. The spring limb support device of claim 1 in which the mounting platform is a stump socket to which the shanks of the limbs are glued into selected position.

22. The spring limb support device of claim 1 in which the mounting platform is a stump socket to which the limbs are permanently supported in a selected position using wrapped bands and adhesive.

23. The spring limb support device of claim 1 in which the mounting platform is provided by a stump socket, at least a portion of the shank of each of the limbs to be supported by stump socket is curved into a general cylindrical concave form to more closely conform to the stump socket and suitable band means placed around the limbs when in selected functioning position against the stump socket and clamp means is provided on the band means to pull the band means firmly against the shanks of the limbs and hold the limbs in fixed position against the stump socket against forces imparted by use.

24. The spring limb support device of claim 23 in which the shank of each of the limbs is provided with a shank slot extending from the end of the limb a predetermined distance and guide means is provided on the stump socket to cooperate with the shank slots to guide and aid proper positioning of the respective limbs.

25. A spring limb support device simulating or supplementing the feel and action during walking of a human foot and lower leg comprising:

a mounting platform for providing connection to the leg of a human wearer;

a pair of monolithic independent limbs, each of which simulates a part of the leg, independently extending to the mounting platform, part of one of which limbs simulates the toe and front part of the foot and part of the other of which simulates the heel of the foot, each of said limbs being composed of resilient spring material and being curved to deform under the weight and dynamic forces of body movement and each being separately cantilever supported on the mounting platform by a terminating support shank such that separate height adjustment of each limb may be made independent of the other limb, the shanks of the respective limbs being spaced from one another so that in the case of each limb, in at least one plane generally in the direction of walking, there is a compound roughly S-shaped curve such that the foot portion of each is a natural termination of the limb approaching the horizontal when worn and at rest in the standing position and having a broad portion simulating, respectively, a toe and front portion of a foot and the heel of the foot.

26. A leg and foot supplementing structure for supplementing during ambulation the feel and action of a human foot and leg comprising:

a mounting platform for providing for connection to the leg of a human wearer;

a pair of monolithic independent limbs, each of which simulates a part of the leg, independently extending to the mounting platform, part of one of which limbs simulates the toe and front part of the foot and part of the other of which simulates the heel of the foot, each of said limbs being composed of resilient spring material and being curved to deform under the weight and dynamic forces of body movement and each being separately cantilever supported on the mounting platform by separate terminating support shank such that separate height adjustment of each limb may be made independent of the other limb, the shanks being spaced apart from one another so that the foot portions cause each limb to respond independently to forces from the ground and react with different separated portions of the mounting platform with a feel to the wearer like that of a normal foot and leg.

27. The leg and foot supplementing structure of claim 26 in which each limb is divided into similar limb portions on each side of the foot each portion having a shank connected to a common band structure providing a mounting platform connected to the leg of the wearer.

28. The leg and foot supplementing structure of claim 27 in which corresponding limb portions on each side of the leg are connected together at the toe and heel respectively.

29. The leg and foot supplementing structure of claim 27 in which the limb portions are composed of flat elements with their width generally paralleling the leg and foot.

30. The leg and foot supplementing structure of claim 28 in which the limb portions are composed of flat elements with their width generally paralleling the leg and foot.

31. The leg and foot supplementing structure of claim 29 in which the common band providing the mounting platform is incorporated into a boot or shoe by which the supplementing structure is connected to the leg of the wearer.

32. The leg and foot supplementing structure of claim 31 in which the toe and heel ends of the limbs respectively are connected to the shoe.

33. The leg and foot supplementing structure of claim 31 in which the heel and toe pieces connecting together limb portions on each side of the foot are made to conform to the shape of the shoe.

* * * * *